US009316569B2

(12) United States Patent
Oh et al.

(10) Patent No.: US 9,316,569 B2
(45) Date of Patent: Apr. 19, 2016

(54) MICRO ELECTRO-MECHANICAL HEATER

(75) Inventors: Yunje Oh, Medina, MN (US); Syed Amanulla Syed Asif, Bloomington, MN (US); Edward Cyrankowski, Woodbury, MN (US); Oden Lee Warren, New Brighton, MN (US)

(73) Assignee: Hysitron, Inc., Eden Prairie, MN (US)

( * ) Notice: Subject to any disclaimer, the term of this patent is extended or adjusted under 35 U.S.C. 154(b) by 0 days.

(21) Appl. No.: 13/510,825

(22) PCT Filed: Aug. 26, 2010

(86) PCT No.: PCT/US2010/046865
§ 371 (c)(1),
(2), (4) Date: Jul. 30, 2012

(87) PCT Pub. No.: WO2011/066018
PCT Pub. Date: Jun. 3, 2011

(65) Prior Publication Data
US 2012/0292528 A1    Nov. 22, 2012

Related U.S. Application Data

(60) Provisional application No. 61/264,753, filed on Nov. 27, 2009.

(51) Int. Cl.
G01N 3/18       (2006.01)
G01N 3/08       (2006.01)
(Continued)

(52) U.S. Cl.
CPC . *G01N 3/08* (2013.01); *H01J 37/20* (2013.01); *G01N 3/18* (2013.01); *G01N 3/42* (2013.01); *G01N 2203/0226* (2013.01); *G01N 2203/0286* (2013.01)

(58) Field of Classification Search
CPC .................................. G01N 3/42; H01J 37/20
USPC ....................................................... 250/443.1
See application file for complete search history.

(56) References Cited

U.S. PATENT DOCUMENTS 3,896,314 A *  7/1975  Nukui et al. ............. 250/442.11
4,491,788 A    1/1985  Zandonatti
(Continued)

FOREIGN PATENT DOCUMENTS

EP        0855452 A1    7/1998
EP     2011066018 A1    6/2011
(Continued)

OTHER PUBLICATIONS

"International Application Serial No. PCT/US2010/046865, Search Report mailed Oct. 28, 2010", 2 pgs.
(Continued)

*Primary Examiner* — Michael Logie
*Assistant Examiner* — James Choi
(74) *Attorney, Agent, or Firm* — Schwegman Lundberg & Woessner, P.A.

(57) ABSTRACT

A sub-micron scale property testing apparatus including a test subject holder and heating assembly. The assembly includes a holder base configured to couple with a sub-micron mechanical testing instrument and electro-mechanical transducer assembly. The assembly further includes a test subject stage coupled with the holder base. The test subject stage is thermally isolated from the holder base. The test subject stage includes a stage subject surface configured to receive a test subject, and a stage plate bracing the stage subject surface. The stage plate is under the stage subject surface. The test subject stage further includes a heating element adjacent to the stage subject surface, the heating element is configured to generate heat at the stage subject surface.

44 Claims, 17 Drawing Sheets

(51) Int. Cl.
*H01J 37/20* (2006.01)
*G01N 3/42* (2006.01)

(56) References Cited

U.S. PATENT DOCUMENTS

| | | | | |
|---|---|---|---|---|
| 4,703,181 | A | * | 10/1987 | Swann et al. ............. 250/442.11 |
| 4,992,660 | A | | 2/1991 | Kobayashi |
| 4,996,433 | A | | 2/1991 | Jones et al. |
| 5,202,542 | A | | 4/1993 | Ferguson |
| 5,331,134 | A | | 7/1994 | Kimura |
| 5,367,171 | A | * | 11/1994 | Aoyama et al. ............. 250/443.1 |
| 5,512,727 | A | | 4/1996 | Myers et al. |
| 5,654,546 | A | | 8/1997 | Lindsay |
| 5,661,235 | A | | 8/1997 | Bonin |
| 5,731,587 | A | * | 3/1998 | DiBattista et al. ......... 250/443.1 |
| 5,821,545 | A | * | 10/1998 | Lindsay et al. ............. 250/443.1 |
| 5,869,751 | A | | 2/1999 | Bonin |
| 6,339,958 | B1 | | 1/2002 | Tsui et al. |
| 6,495,838 | B1 | * | 12/2002 | Yaguchi et al. ............. 250/443.1 |
| 6,520,004 | B1 | | 2/2003 | Lin |
| 7,274,450 | B1 | | 9/2007 | Green |
| 7,451,636 | B2 | * | 11/2008 | Bradshaw et al. ................. 73/83 |
| 7,685,868 | B2 | | 3/2010 | Woirgard et al. |
| 8,569,714 | B2 | * | 10/2013 | Han et al. ................. 250/440.11 |
| 8,631,687 | B2 | | 1/2014 | Patten et al. |
| 8,844,368 | B2 | * | 9/2014 | Peecock et al. ................. 73/827 |
| 2002/0110177 | A1 | | 8/2002 | Nakayama et al. |
| 2006/0025002 | A1 | | 2/2006 | Zhang et al. |
| 2006/0180577 | A1 | | 8/2006 | Lindeman |
| 2007/0278420 | A1 | | 12/2007 | Molhave |
| 2008/0092938 | A1 | | 4/2008 | Majumdar et al. |
| 2008/0276727 | A1 | * | 11/2008 | Enoksson et al. .......... 73/862.68 |
| 2008/0290290 | A1 | * | 11/2008 | Nagakubo et al. ......... 250/443.1 |
| 2009/0111701 | A1 | | 4/2009 | Ahn et al. |
| 2009/0120172 | A1 | | 5/2009 | Bradshaw et al. |
| 2009/0194689 | A1 | | 8/2009 | Abramson et al. |
| 2009/0206258 | A1 | * | 8/2009 | Kasai et al. .................... 250/311 |
| 2009/0289050 | A1 | | 11/2009 | Ondricek |
| 2010/0095780 | A1 | | 4/2010 | Oh et al. |
| 2010/0132441 | A1 | | 6/2010 | Oh et al. |
| 2010/0180356 | A1 | | 7/2010 | Bonilla et al. |
| 2010/0186520 | A1 | * | 7/2010 | Wheeler et al. ................. 73/818 |
| 2010/0212411 | A1 | | 8/2010 | Passilly et al. |
| 2010/0294147 | A1 | | 11/2010 | Loiret-bernal et al. |
| 2011/0107472 | A1 | | 5/2011 | Han et al. |
| 2011/0152724 | A1 | | 6/2011 | Hansma et al. |
| 2011/0252874 | A1 | * | 10/2011 | Patten et al. ........................ 73/81 |
| 2011/0277555 | A1 | | 11/2011 | Peecock et al. |
| 2011/0277556 | A1 | | 11/2011 | Peecock et al. |
| 2014/0326707 | A1 | | 11/2014 | Schmitz et al. |
| 2014/0331782 | A1 | | 11/2014 | Keranen et al. |
| 2015/0033835 | A1 | | 2/2015 | Asif et al. |
| 2015/0179397 | A1 | * | 6/2015 | Damiano et al. ............... 250/440 |
| 2015/0185117 | A1 | | 7/2015 | Schmitz et al. |

FOREIGN PATENT DOCUMENTS

| | | | | |
|---|---|---|---|---|
| GB | | 2116459 | A * | 9/1983 |
| JP | | 4996867 | U | 8/1974 |
| JP | | 55088256 | A | 7/1980 |
| JP | | 6327731 | A | 3/1983 |
| JP | | 58173159 | U | 11/1983 |
| JP | | 01081553 | U | 5/1989 |
| JP | | 04131741 | A | 5/1992 |
| JP | | 0566186 | A | 3/1993 |
| JP | | 0572457 | A | 3/1993 |
| JP | | 2002318318 | A | 10/2002 |
| JP | | 2009526230 | A | 7/2009 |
| JP | | 2009193833 | A | 8/2009 |
| JP | | 2015501935 | A | 1/2015 |
| WO | WO-2008061224 | | | 5/2008 |
| WO | WO-2011104529 | A1 | | 9/2011 |
| WO | WO-2013074623 | A1 | | 5/2013 |
| WO | WO-2013082145 | A1 | | 6/2013 |
| WO | WO-2013082148 | A1 | | 6/2013 |
| WO | WO-2013187972 | A1 | | 12/2013 |

OTHER PUBLICATIONS

"International Application Serial No. PCT/US2010/046865, Written Opinion mailed Oct. 28, 2010", 8 pgs.

Allard, L. F., et al., "A New Paradigm for Ultra-High-Resolution Imaging at Elevated Temperatures", Microsc. Microanal 14(Suppl 2), (2008), 792-793.

Briceno, M., et al., "In-situ TEM Observations on the Sintering Process of Colloidal Gold Using an Ultra-fast Heating Stage", Microsc Microanal 14(Suppl 2), (2008), 1336-1337.

Damiano, John, "A MEMS-based Technology Platform for in-situ TEM Heating Studies", Microsc Microanal 14(Suppl 2), (2008), 1332-1333.

Eakins, D. E., et al., "An in situ TEM study of phase formation in gold-aluminum couples", Journal of Materials Science 39, (2004), 165-171.

Kamino, T., et al., "A newly developed high resolution hot stage and its application to materials characterization", Microsc. Microanal. Microstruct. 4, (1993), 127-135.

Kamino, T., et al., "In-situ high-resolution electron microscopy study on a surface reconstruction of Au-deposited Si at very high temperatures", Philosophical Magazine A 75(1), (1997), 105-114.

Min, K.-H., et al., "Crystallization behaviour of ALD-Ta2O5 thin films: the application of in-situ TEM", Philosophical Magazine 85(18), (Jun. 21, 2005), 2049-2063.

Saka, H., "In situ observation of solid-liquid interfaces by transmission electron microscopy", J. Mater. Res. 20(7), (Jul. 2005), 1629-1640.

Saka, H., "In-situ TEM observation of transformation of dislocations from shuffle to glide sets in Si under supersaturation of interstitials", Philosophical Magazine 86(29-31), (Oct.-Nov. 2006), 4841-4850.

Tsukimoto, S., et al., "In situ high resolution electron microscopy/electron energy loss spectroscopy observation of wetting of a Si surface by molten Al", Journal of Microscopy 203, Pt. 1, (Jul. 2001), 17-21.

Wu, Yiying, et al., "Direct Observation of Vapor—Liquid—Solid Nanowire Growth", J. Am. Chem. Soc. 2001(123), (Mar. 13, 2001), 3165-3166.

"U.S. Appl. No. 13/090,036, Notice of Allowance mailed Mar. 19, 2013", 8 pgs.

"International Application Serial No. PCT/US2010/046865, International Preliminary Report on Patentability mailed May 30, 2012", 10 pgs.

"International Application Serial No. PCT/US2012/065009, International Search Report mailed Jan. 25, 2013", 2 pgs.

"International Application Serial No. PCT/US2012/065009, Written Opinion mailed Jan. 25, 2013", 5 pgs.

"International Application Serial No. PCT/US2012/066842, International Search Report mailed Feb. 7, 2013", 2 pgs.

"International Application Serial No. PCT/US2012/066842, Written Opinion mailed Feb. 7, 2013", 8 pgs.

"International Application Serial No. PCT/US2012/066846, International Search Report mailed Feb. 6, 2013", 2 pgs.

"International Application Serial No. PCT/US2012/066846, Written Opinion mailed Feb. 6, 2013", 8 pgs.

"International Application Serial No. PCT/US2013/031650, International Search Report mailed May 31, 2013", 2 pgs.

"International Application Serial No. PCT/US2013/031650, Written Opinion mailed May 31, 2013", 4 pgs.

"U.S. Appl. No. 13/090,036, Notice of Allowance mailed Jul. 15, 2013", 9 pgs.

"European Application Serial No. 12849761.7, Office Action mailed Jun. 27, 2014", 3 pgs.

"European Application Serial No. 12853899.8, Office Action mailed Jul. 10, 2014", 2 pgs.

"Japanese Application Serial No. 2012-541077, Response filed Jun. 17, 2014", with English translation of claims, 10 pgs.

"U.S. Appl. No. 14/358,065, Preliminary Amendment filed May 14, 2014", 8 pgs.

(56) References Cited

OTHER PUBLICATIONS

"U.S. Appl. No. 14/361,094, Preliminary Amendment filed May 28, 2014", 8 pgs.
"U.S. Appl. No. 14/361,133, Preliminary Amendment filed May 28, 2014", 8 pgs.
"Application Serial No. PCT/US2012/065009, Article 19 Amendment filed Mar. 25, 2013", 6 pgs.
"European Application Serial No. 10833722.1, Preliminary Amendment filed Jan. 21, 2013", 21 pgs.
"International Application Serial No. PCT/US2012/065009, Supplemental Article 19 Amendment filed Apr. 26, 2013", 12 pgs.
"International Application Serial No. PCT/US2012/065009, International Preliminary Report on Patentability mailed May 30, 2014", 7 pgs.
"International Application Serial No. PCT/US2012/066842, Demand and Response filed Sep. 27, 2013 to Written Opinion mailed Feb. 7, 2013", 25 pgs.
"International Application Serial No. PCT/US2012/066842, International Preliminary Report on Patentability mailed Jun. 12, 2014", 10 pgs.
"International Application Serial No. PCT/US2012/066842, International Preliminary Report on Patentability mailed Dec. 6, 2013", 36 pgs.
"International Application Serial No. PCT/US2012/066846, Demand and Response filed Sep. 27, 2013 to Written Opinion mailed Feb. 6, 2013", 26 pgs.
"International Application Serial No. PCT/US2012/066846, International Preliminary Report on Patentability mailed Dec. 3, 2013", 16 pgs.
"Japanese Application Serial No. 2012-541077, Office Action mailed Mar. 18, 2014", w/English translation, 4 pgs.
"International Application Serial No. PCT/US2013/031650, International Preliminary Report on Patentability mailed Dec. 24, 2014", 6 pgs.
"Japanese Application Serial No. 2012-541077, Office Action mailed Jan. 6, 2015", with English translation of claims, 4 pgs.
"Japanese Application Serial No. 2014-541415, Office Action mailed Dec. 2, 2014", with English translation of claims, 6 pgs.
"U.S. Appl. No. 14/358,065, Non Final Office Action mailed Jul. 31, 2015", 12 pgs.
"U.S. Appl. No. 14/358,065, Response filed Jun. 17, 2015 to Restriction Requirement mailed Apr. 20, 2015", 14 pgs.
"U.S. Appl. No. 14/358,065, Restriction Requirement mailed Apr. 20, 2015", 7 pgs.
"European Application Serial No. 12853899.8, Extended European Search Report mailed Jun. 29, 2015", 9 pgs.
"Japanese Application Serial No. 2015-517243, Office Action mailed Jun. 16, 2015", 9 pgs.
"U.S. Appl. No. 14/358,065, Final Office Action mailed Nov. 18, 2015", 10 pgs.
"European Application Serial No. 12853965.7, Extended European Search Report mailed Nov. 16, 2015", 10 pgs.
"Japanese Application Serial No. 2015-517243, Final Office Action mailed Dec. 1, 2015", W/ English translation, 5 pgs.
"U.S. Appl. No. 14/358,065, Response filed Oct. 28, 2015 to Non Final Office Action mailed Jul. 31, 2015", 12 pgs.
"U.S. Appl. No. 14/407,783, Preliminary Amendment filed Dec. 12, 2014", 13 pgs.
"European Application Serial No. 12849761.7, Extended European Search Report mailed Aug. 7, 2015", 7 pgs.
"European Application Serial No. 12853965.7, Non Final Office Action mailed Sep. 9, 2015", 5 pgs.
"Japanese Application Serial No. 2014-541415, Response Office Action mailed Dec. 2, 2014", W/ English Claims, 6 pgs.
"European Application Serial No. 12853899.8, Response filed Jan. 26, 2016 to Extended European Search Report mailed Jun. 29, 2015", 12 pgs.
"European Application Serial No. 13804048.0, Extended European Search Report mailed Feb. 9, 2016", 6 pgs.

\* cited by examiner

MICRO ELECTRO-MECHANICAL HEATER

RELATED APPLICATIONS

This patent application is a U.S. National Stage Filing under 35U.S.C. 371from International Patent Application Serial No. PCT/US2010/046865, filed Aug. 26, 2010, and published on Jun. 3, 2011 as WO 2011/066018A1, which claims the benefit of priority to U.S. Provisional Application Ser. No. 61/264,753, filed on Nov. 27, 2009, which applications and publication are incorporated herein by reference in their entirety.

SBIR NOTICE

This invention was made with Government support under (DE-FG02-07ER84812) awarded by the Department of Energy. The Government has certain rights in this invention

TECHNICAL FIELD

Sub-micron scale testing.

BACKGROUND

Nanoindentation is a method to quantitatively measure mechanical properties, such as elastic modulus and hardness, of materials at nanometer length scale using depth sensing indentation technique. In nanoindentation, a nanoindenter capable of determining the loading force and displacement is used Typically, a force employed in nanoindentation is less than 10 mN, with a typical displacement range being smaller than 10 µm, and with a noise level typically being better than 1 nm rms. The force and displacement data are used to determine a sample's mechanical properties. For sample property estimation a nanoindenter is integrated with a characterized indenter tip which has known geometry and known mechanical properties.

One of the emerging nanomechanical characterization techniques is quantitative transmission electron microscopy (TEM) in-situ mechanical testing. This testing method enables monitoring of the deformation of a sample in real time while measuring the quantitative mechanical data. Coupling a nanomechanical system with TEM imaging allows researchers to study structure property correlation and the influence of pre-existing defects on the mechanical response of materials. In addition to imaging, selected-area diffraction can be used to determine sample orientation and loading direction influence on mechanical response. Moreover, with in-situ mechanical testing, the deformation can be viewed in real-time rather than "post mortem". Performing TEM in-situ nanomechanical testing can provide unambiguous differentiation between the many possible causes of force or displacement transients which may include dislocation bursts, phase transformations, shear banding or fracture onset. Nanomechanical testing at elevated temperature is an important part of material characterization for materials having phase changes or variant mechanical properties as the temperature increases. Some of the applications of the high temperature nanomechanical test are glass transition temperature identification of polymeric and rubber materials, phase transformations of low temperature metals and shape memory alloys, study of biological samples at body temperature, simulated and accelerated thermal aging studies, accelerated material creep studies, and time-temperature-superposition curve plotting of polymers.

DESCRIPTION OF THE EMBODIMENTS

In the following detailed description, reference is made to the accompanying drawings which form a part hereof, and in which is shown by way of illustration how specific embodiments of the present disclosure may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. These embodiments are described in sufficient detail to enable those skilled in the art to practice aspects of this disclosure, and it is to be understood that other embodiments may be utilized and that structural changes may be made without departing from the scope of the present disclosure. Therefore, the following detailed description is not to be taken in a limiting sense, and the scope of the present disclosure is defined by the appended claims and their equivalents.

According to embodiments described herein, a system and method are provided for mechanically testing small test subjects at the nano and micro scales (i.e., sub-micron scale), including, but not limited to, nanostructures, thin films and the like. Such testing is performed, in one example, to determine the mechanical properties of the materials composing the subjects. A TEM holder modification for nanomechanical testing instrumentation provides a small space constrained by the front end portion of the holder and the pole gap of a TEM electron beam. Developing a TEM in-situ nanomechanical test instrument with an integrated heater is therefore a great challenge requiring a new design and instrumentation approach. According to one embodiment, as will be described in greater detail herein, the system described herein includes a micromachined or microelectro-mechanical (MEMS) based heater including heating and sensing elements. The heater enables the use of a nanoindenter or other instrument which provides a high precision actuation force, corresponding indenting or other deformation (e.g., indenting, scratching, pulling, compressing and the like), and high resolution displacement sensing on at least a nanometer or micrometer scale.

Figure 1:
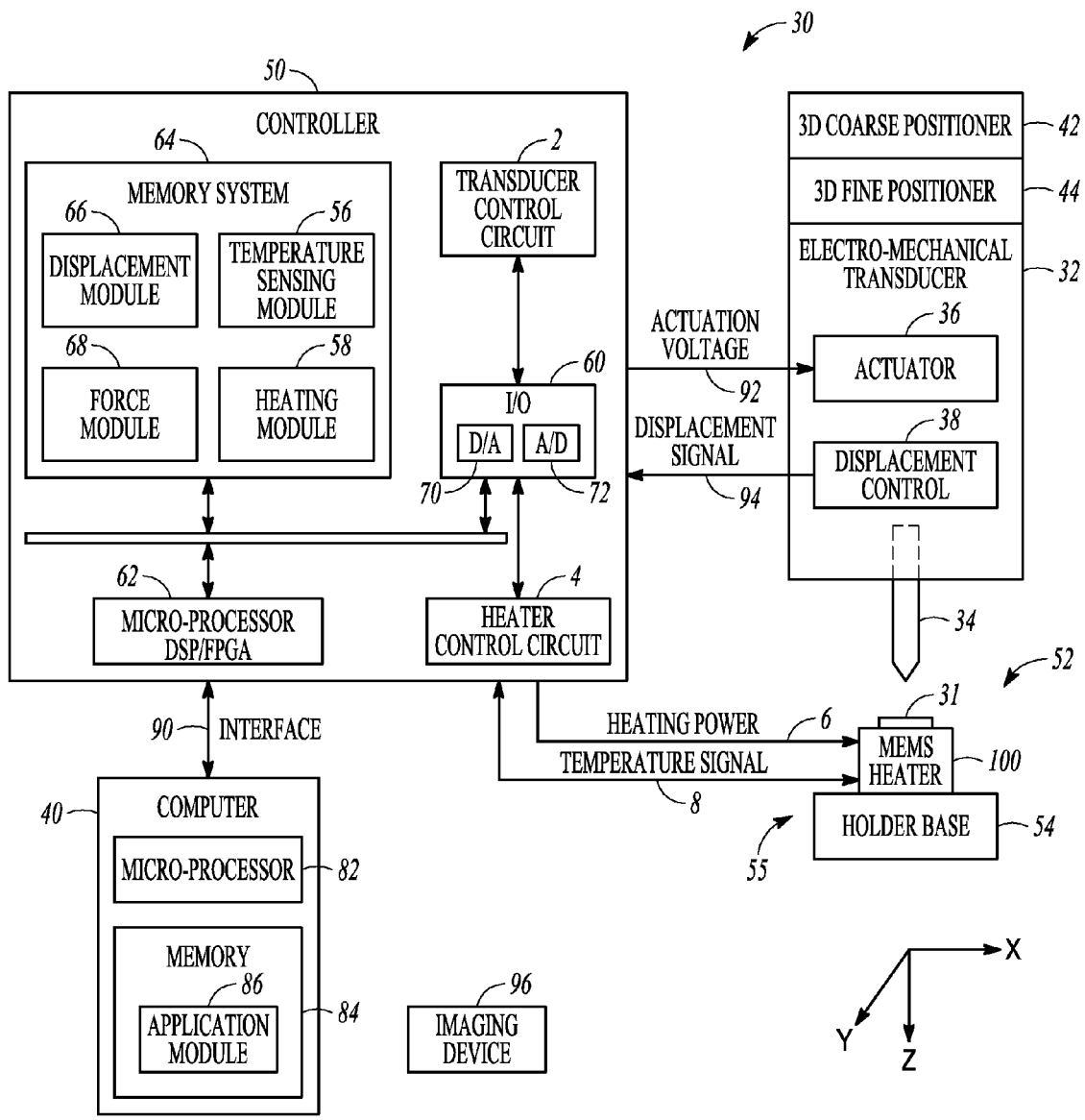
FIG. 1 is a block diagram showing one example of a nanomechanical test system.

FIG. 1 is a schematic block diagram illustrating an example of a nanomechanical test system 30 employing a MEMS based heater 100 (referred to hereafter as MEMS heater 100) for heating and sensing the temperature of a small test sample 31. In addition to the MEMS heater 100, the nanomechanical test system 30 (e.g., sub-micron) includes an electro-mechanical (EM) transducer 32 having a displaceable probe 34, an actuator 36 to displace the probe 34, a displacement sensor 38, a computer 40, a coarse positioner 42, a fine positioner 44, and a controller 50. The EM transducer 32 includes, but is not limited to, indentation, compression, tensile, fatigue, tribology, fracture instruments and the like.

The nanomechanical test system 30 further includes a test subject holder 55 including a sample stage 52 and having a base portion 54 (a holder base). The MEMS heater 100 is positioned on the sample stage 52 (e.g., within or along the subject holder), and the holder is detachably mounted to the nanomechanical test system 30. According to one embodiment, and described in greater detail below, the MEMS heater 100 is micromachined or MEMS based so as to fit into a small, restricted space such as for in-situ nanomechanical testing application within a quantitative transmission electron microscope (TEM), for example.

According to one embodiment, the controller 50 includes an input/output module 60, a transducer control circuit 2, a heater control circuit 4, a processor 62, such as microprocessor or digital signal processor (DSP) and/or field programmable gate array (FPGA), for example, and a memory system 64. According to one embodiment, the memory system 64 includes a displacement module 66, a force module 68, a temperature sensing module 56, and a heating module 58. According to another embodiment, the input/output module 60 further includes a D/A converter 70, and an A/D converter 72.

In one example, the computer 40 includes a processor 82 and a memory system 84 that stores an application module 86. The computer 40 may access and communicate with the controller 50 via an interface 90 (e.g. a USB interface). FIG. 1 shows the computer 40 and controller 50 as separate entities. In other examples, computer 40 and controller 50 are combined as part of a single processing and control system.

According to one embodiment, the application module 86, displacement module 66, and force module 68 each include instructions respectively stored in memories 64 and 84 and which are accessible and executable by processor 62. Memories 64 and 84 include, but are not limited to, any number of volatile or non-volatile storage devices such as RAM, flash memory, hard disk drives, CD-ROM drives, DVD drives and the like. In other embodiments, the displacement module 66, force module 68, temperature sensing module 56, and heating module 58 include any combination of hardware and software components configured to perform functions described herein. The software component of the displacement module 66 and the force module 68, the temperature sensing module 56, and the heating module 58 are each stored on a medium separate from the processing system 62 prior to being stored in memory system 64, in one example. Examples of such media include a hard disk drive, a flash memory device, a compact disc (e.g. a CD-ROM, CD-R, or CD-RW), and a digital video disc (e.g. a DVD, DVD-R, and DVD-RW), for example.

According to one embodiment, the coarse positioner 42 and the fine positioner 44 enable 3-dimensional positioning (i.e. x-, y-, and z-axes in FIG. 1) of the EM transducer 32 and displaceable probe 34 in the millimeter range with a sub-nanometer resolution. According to one embodiment, final positioning and movement of the displaceable probe 34 is performed by the actuator 36 via the application module 86 on the computer 40 and the controller 50. According to one embodiment, the controller 50 is configured to control and monitor the movement of displaceable probe 34 and to provide data representative of a displacement of the displaceable probe 34 (from the displacement sensor 38) to the computer 40 through the interface 90. According to one embodiment, controller 50 is configured to determine and adjust a force applied to the test sample 31 by the displaceable probe 34.

According to one embodiment, the controller 50 is configured to control and monitor the temperature of the MEMS heater 100 and the test subject 31 and to provide data representative of a temperature of the MEMS heater 100 and the test subject 31 to the computer 40 via interface 90. In one example, the controller 50 is configured to determine and adjust a heating power 6 applied to the MEMS heater 100 and the test subject 31 to achieve a desired test subject temperature (and heater temperature) for testing and observation of the test subject.

In operation, a user can program the controller 50 with the computer 40 through the application module 86. According to one embodiment, the controller 50, through the force module 68, provides an input or force signal 92 to the actuator 36 representative of a desired force for application to the test sample 31 by the displaceable probe 34. In response to the input actuation force signal 92, the actuator 36 drives the displaceable probe 34 toward the sample stage 52 (e.g. along the z-axis in FIG. 1). The displaceable probe 34 contacts and applies the desired force to the test subject 31. The D/A converter 70 converts the input or force signal provided by the force module 68 from digital analog form which, in turn, is amplified to generate the actuation force 92 by transducer control circuit 2 as provided to actuator 36.

The displacement sensor 38 comprises a transducer (e.g. a capacitive transducer) which detects movement of displaceable probe 34 at least along the z-axis, and provides a displacement signal 94 to controller 50 representing measurement of the movement of the displaceable probe 34. In other embodiments, in addition to movement along the z-axis, the displacement sensor 38 detects and provides indication of other types of movement of displaceable probe 34, such as displacement along the x- and/or y-axes or rotational movement about the x- and/or y-axes. The transducer control circuit 2 conditions the displacement signal 94 from the displacement sensor 38 and sends the displacement signal 94 to the A/D converter 72. The A/D converter 72 converts the displacement signal 94 from an analog form, as received from the transducer control circuit 2, to a digital form for processing by the displacement module 66. The displacement module 66, according to one embodiment, communicates measurement of the movement of the displaceable probe 34 to the force module 68 (e.g. for force calculations) and computer 40 (via interface 90).

According to one embodiment, controller 50 is further configured to control movement or displacement of displaceable probe 34 in the x- and y-directions relative to sample stage 52, such as by moving EM transducer 32 relative to sample stage 52 or by moving sample stage 52 relative to EM transducer 32. According to one embodiment, the nanomechanical test system 30 further includes an imaging device 96 comprising an instrument/device such as an electron microscope, an optical microscope, or a scanning probe microscope (SPM) (e.g., an atomic force microscope (AFM)) configured to provide images of a test sample 31 mounted to sample stage 52, including images of the test subject before, during and after mechanical testing such as indentation, compression, fatigue and fracture testing and the like and video of the same.

Examples of nanomechanical test systems suitable to be configured for use with a MEMS heater 100 according to embodiments of the present disclosure are described in U.S. Pat. Nos. 5,553,486 and 5,869,751, both of which are assigned to the same assignee as the present disclosure and incorporated herein by reference. For instance, test systems suitable for configuration with the MEMS heater 100 include, but are not limited to, optical microscopes, scanning probe microscopes (SPM), electron microscopes and the like. In each of these examples, ex-situ or in-situ heating is performed with the MEMS heater 100. Another test system suitable for configuration with the MEMS heater 100 is an electron microscopy (e.g. transmission electron (TEM) and/or scanning electron (SEM)) in-situ nanomechanical tester commercially available under the trade name PicoIndenter from Hysitron, Incorporated, of Minneapolis, Minn., USA.

During a temperature controlled mechanical testing, as will be described in greater detail below, MEMS heater 100 is controlled so as to heat and maintain the test subject 31 at the desired temperature. The MEMS heater 100 is operated with at least one of open loop control or closed loop control. For more accurate temperature regulation in a changing thermal environment, the closed loop control system utilizing the temperature signal 8 as the feedback is used. When the sample temperature reaches the desired temperature, EM transducer 32 is operated to apply a force with the moveable probe 34 to the test subject 31. According to one embodiment, the temperature of the test subject 31 is measured by the MEMS heater 100 and the force applied and a displacement of the indented material of the test subject 31 are measured by nanomechanical test system 30. The nanomechanical test system 30 measures these parameters through the actuator 36 and the displacement sensor 38 of EM transducer 32 while being synchronously imaged via imaging device 96. The force and displacement data and images of the corresponding indentation are substantially simultaneously measured in real-time and observed by a combination of the actuator 36, the displacement sensor 38 and the imaging device 96 (e.g., an electron microscope). Stated another way, examination of the test subject—through the above described measuring and imaging techniques—at a specified testing temperature is thereby performed without any appreciable pause between measurement, imaging or heating. Phenomena including elastic/plastic deformation and the like that alter the shape of the indentation over time after application of the indentation force have minimal effect on the measurement and imaging of the indentation. Additionally, elastic/plastic deformation and the like are observable and measurable for a time period starting immediately after indentation. That is to say, because the nanomechanical test system 30 with the MEMS heater 100 is able to perform the indentation testing, and measure and observe the material surrounding the indentation at substantially the same time, changes in the material over a period of time are similarly observable at the time of and immediately after the indentation. Observation of these parameters and phenomena at or immediately after indentation are sometimes critical in the accurate assessment and determination of corresponding material properties.

Figure 2A:
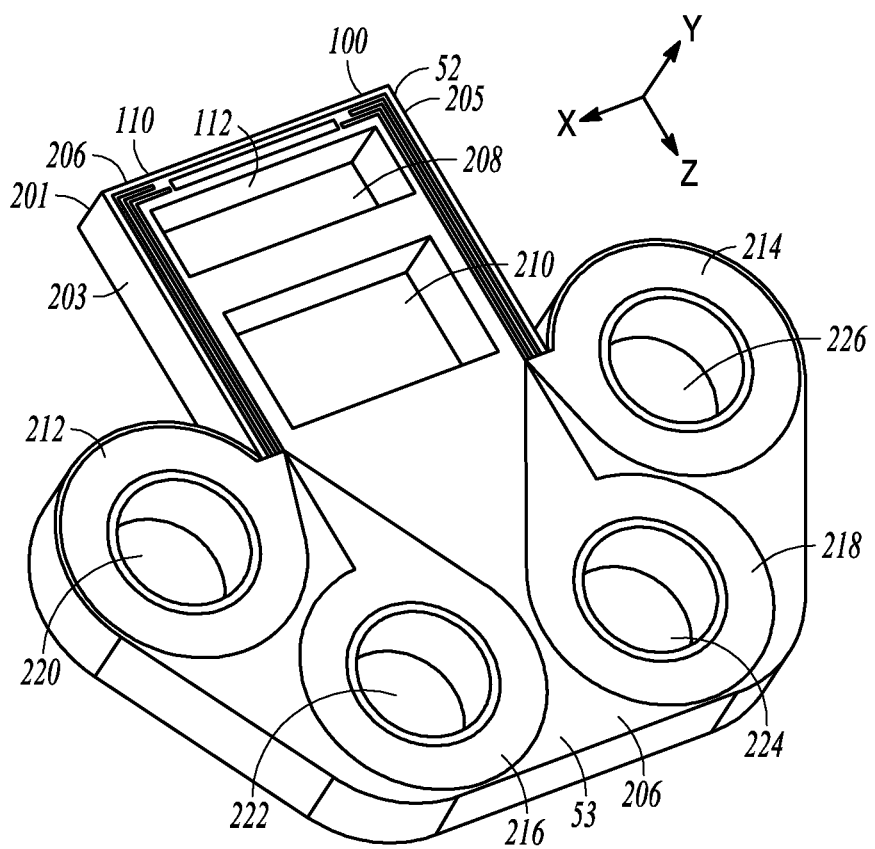
FIG. 2A is a perspective view showing one example of a sample stage and MEMS heater.

FIGS. 2A, B show the MEMS heater 100 designed for nanomechanical testing at a selected elevated temperature. The MEMS heater 100, for instance, in the sample stage 52, is coupled with the base portion 54 as described above and further described below. As shown in FIG. 2, in one example, the sample stage 52 includes a base interface 53 for coupling with the base portion 54 (i.e., the holder base, further described below) to form the test subject holder 55. The sample stage 52 further includes a test subject stage 110. For nanomechanical tests at elevated temperature, the MEMS heater 100 mounts a test subject 31 (shown in FIG. 1) at the test subject stage 110 for interaction with the displaceable probe 34. As an example, a thin film subject is attached to the MEMS heater 100 (e.g., the test subject stage 110) along a stage subject surface 201 and positioned perpendicular to the Z-axis for a nanoindentation experiment. For proper sample mounting, the stage subject surface 201 should be flat and perpendicular to the Z-axis. As described in further detail below the stage subject surface 201 is coupled with a stage plate 112. The stage plate 112 braces the stage subject surface 201 providing mechanical stiffness and minimizes deflection of the stage subject surface during mechanical testing of a sample.

Figure 2B:
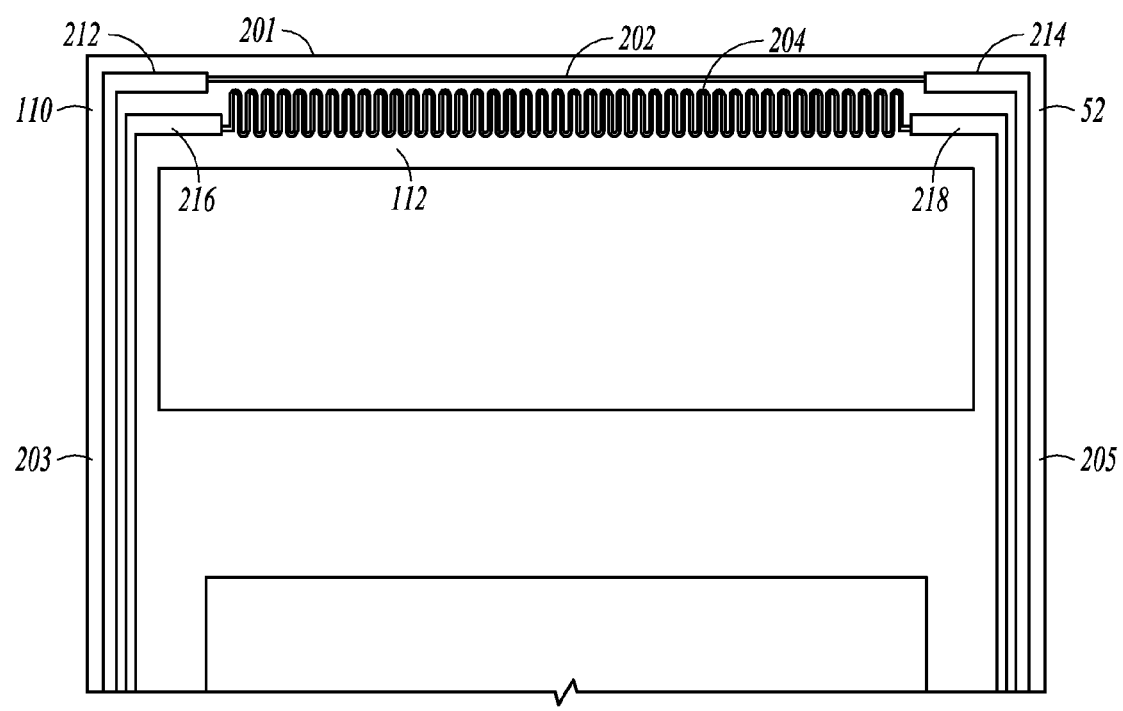
FIG. 2B is a detailed view of the MEMS heater and sample stage shown in FIG. 2A.
Figure 6A:
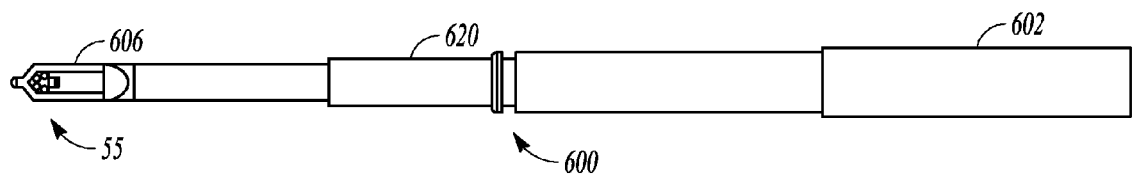
FIG. 6A is a side view of one example of a test subject holder including a sample stage with a MEMS heater.
Figure 6B:
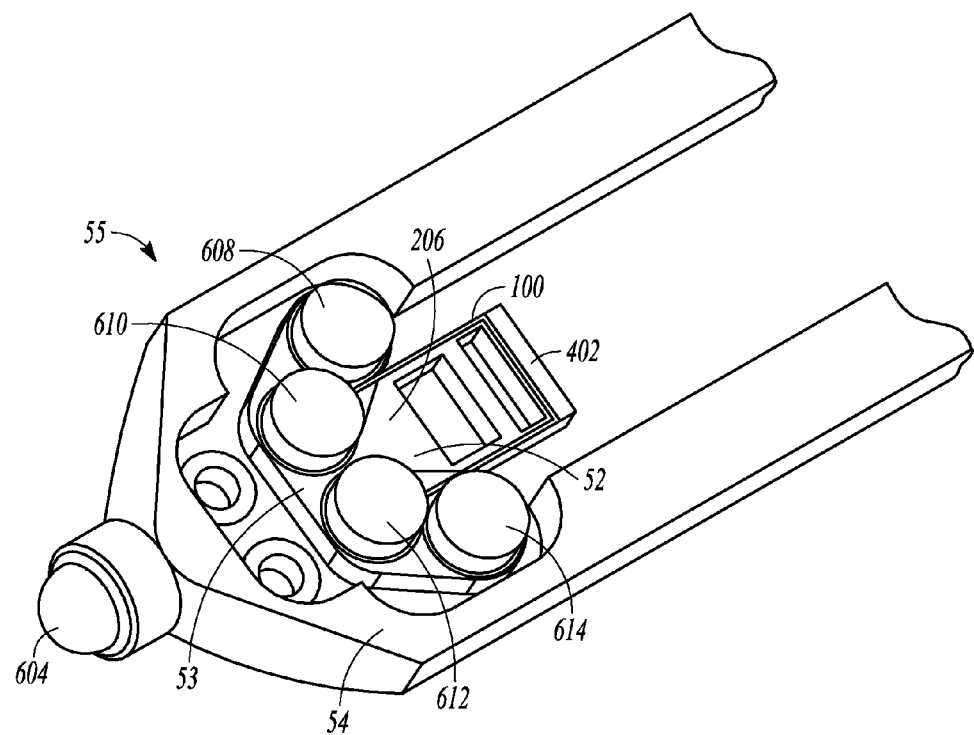
FIG. 6B is a detailed perspective view of the test subject holder and sample stage shown in FIG. 6A.

The heating element 202 and the sensing element 204 are thin film resistors within a substrate 206 of the MEMS heater 100. As shown in FIG. 2B, the heating and sensing elements 202, 204 are on the test subject stage 110 adjacent to the stage subject surface 201. Stated another way, relative to the base portion 54 (FIG. 6B) and the base interface 53, the heating element 202 and sensing element 204 are immediately adjacent to the stage subject surface 201 to ensure heat is generated and temperature is measured at a test subject and not transmitted through large portions of the sample stage 52 to a test subject 31. As described below, minimizing the distance heat is transmitted through the sample stage 52 to the test subject correspondingly minimizes mechanical drift and thermal expansion. Similarly, positioning of the heating element 202 remotely from the base portion 54, as shown in FIG. 6B, thermally isolates the heated test subject stage 110 from the remainder of the test subject holder 55 and further minimizes drift and expansion. Referring to FIG. 2B, positioning the heating element 202 adjacent to the stage subject surface 201 on the test subject stage 110 and away from the base interface 53 (coupled to the base portion 54 shown in FIG. 6B) remotely positions the heating element from the rest of the test subject holder 55.

The heating element 202 is heated by generating heating power using current flow. The sensing element 204 senses temperature in the substrate 206 by corresponding resistance variation with temperature changes. As heating element 202 and sensing element 204 materials, metal or ceramic thin films are used. The heating element 202 and the sensing element 204 are connected to the base portion 54 of the sample stage 52 using thin-film leads 212, 214, 216 and 218. The thin film electrical leads 212, 214, 216 and 218 include one or more of metal materials, ceramic materials and the like. The electrical leads 212, 214, 216 and 218 have relatively low electrical resistance because the heating element 202 and the sensing element 204 should be the dominant resistance source. By using low electrical resistivity materials (e.g., gold), thin film leads 212, 214, 216 and 218 have correspondingly low resistance. The low resistance of the heater leads 212 and 214 prevents heat generation on the leads. Similarly, the low resistance of the sensor leads 216 and 218 prevents the addition of undesirable resistance corresponding to locations on the sample stage remote from the stage subject surface 201 and the heating element 202 for temperature measurements of the MEMS heater 100.

The control voltage is provided by the D/A converter 70 to control the current flow though the heater control circuit 4 and the sensing element 204. The heater control circuit 4 uses either DC or AC circuitry for the resistance measurement of the sensing element 204. Since the sensing element 204 temperature change is detected by a change in resistance, for resistance detection, a Wheastone Bridge is used for the sensing circuitry in one example.

Nanomechanical testing at elevated temperature experiences thermal expansion and drift proportional to the volume and length of the materials involved (the tested sample 31 as well as the sample stage 52). Since mechanical testing relies on measured force and displacement data, thermal expansion and mechanical drift cause undesirable change in the displacement measurement data (and force calculation) and distort the mechanical properties calculated from the measured data. To minimize thermal expansion and mechanical drift, a material with low coefficient of thermal expansion and a large thermal resistance from the heating element 202 of the sample stage 52 to the base portion 54 of the test subject holder 55 are required. The MEMS heater 100 is designed to create a large temperature drop through the heating element 202 to the base portion 54 (see FIG. 1) to minimize thermal expansion and drift within the components. To have an enhanced temperature drop from the heating element 202 to the base portion 54, the MEMS heater 100 includes the exemplary geometry shown in FIG. 2 and the materials described herein having a large thermal resistance between the heating element 202 and the base portion 54. Additionally, the materials of the sample stage 52 and at least the support columns 203, 205 have low coefficients of thermal expansion, and any thermal drift and expansion because of heating are thereby minimized within the sample stage 52.

With the large temperature drop in the MEMS heater 100 from the heating element 202 to the base portion 54, the heated volume is limited to the portion of the MEMS heater close to heating element 202 (e.g., the stage subject surface 201 and to a much smaller extent the support columns 203, 205 shown in FIG. 2A). The heated volume is thereby minimized and the associated thermal expansion and drift is thereby minimized throughout the test subject holder 55 including the sample stage 52 and the base portion 54 (see FIG. 1). Minimizing the heated volume of the MEMS heater 100 also minimizes power used to heat the test sample 31 to a desired temperature since heat conduction and convection are limited to a smaller heating volume (i.e., the test subject stage 110 including the stage subject surface 201 and the stage plate 112 and to a lesser degree the support columns 203, 205 and the base interface 53). Concentrating the application of heat to the test subject stage 110 including the stage subject surface 201 also causes less thermal expansion and drift since less energy is involved in the heating process. That is to say, the geometry of the sample stage 52, the materials used therein and the location of the heating element 202 alone or together localize heating within the sample stage to the test subject stage 110. Stated another way, the materials and geometry of the sample stage 52 and the MEMS heater 100 (e.g., the support columns 203, 205) throttle heat transfer from the sample stage 52 into larger components of the test subject holder 55 (see FIGS. 6A, B) and even the base interface 53 otherwise capable, at elevated temperatures, of greater expansion and thermal drift because of their relatively large volume and dimensions compared to the test subject stage 110 of the sample stage 52.

To increase the thermal resistance and correspondingly decrease heat transfer through the test subject holder 55, the sample stage 52 includes a material having low thermal conductivity and a minimized cross-sectional area (an area perpendicular to the Z-axis and the direction of heat transfer in the example shown in FIGS. 2A, B). The thermal resistance of the material is inversely proportional to both the material thermal conductivity and the cross-sectional surface area perpendicular to a heat flux direction (e.g., the direction of heat transfer along the support columns 203, 205 from the heater 100 toward the base portion 54). The MEMS heater 100 shown in FIG. 2 employs voids 208 and 210 with the support columns 203, 205 having minimal cross sectional area relative to the area of the test subject stage 110 to reduce the cross-sectional area perpendicular to the Z-axis and enhance the thermal resistance along the Z-axis. The increased thermal resistance enhances the temperature drop from the heating element 202 through the sample stage 52 when the MEMS heater 100 is operated.

Use of low thermal conductivity material for the sample stage 52, the geometry of the stage (e.g., columns and voids), and the location of the heating element 202 adjacent to the stage subject surface 201 ensures heating of a test sample occurs at the test sample, and heat energy is minimally transmitted through the remainder of the sample stage 52 and into the test subject holder, such as the holder base 54. Because heat is generated at the test subject stage 110 adjacent to a test sample on the stage subject surface 201 heat energy must travel through the minimally thermal conductive material of the test subject stage 110 and the minimal cross sectional area of the support columns 203, 205 to reach portions of the test subject holder 55 having larger volumes and correspondingly capable of large mechanical drift and thermal expansion. Further, only minimal radiant heat from the test subject stage 110 can cross the voids 208, 210 relative to conductive heat transfer through the columns 203, 205. The voids 208, 210 thereby cooperate with the other resistive heat transfer features of the sample stage 52 to throttle heat transfer away from the test subject stage 110. These features alone or in combination thermally isolate (e.g., substantially or extensively thermally insulate) the test subject stage 110 and substantially contain heat generated therein relative to the holder base 54 and the remainder of the test subject holder 55 to minimize mechanical drift and thermal expansion through heating of the heating element 202. A minimal amount of heat is transferred to portions of the test subject holder 55 (as described below by example). In one example, the holder base 54 and the base interface 53 (FIGS. 2A and 6B) are at a temperature of around 50 degrees Celsius or less (e.g., around 20 degrees Celsius) while the test subject stage 110 is heated to around 400 degrees Celsius. While complete thermal isolation is not achieved, heat transferred to the base interface 53, the holder base 54 and the remainder of the test subject holder 55 from the heated test subject stage 110 is minimal and mechanical drift and thermal expansion are correspondingly minimal. Samples (e.g., sample 31) on the stage subject surface 201 are thereby held substantially static during heating, mechanical testing and observation, for instance, with a transmission electron microscope. Stated another way, observation of a micron or nanometer size discrete portion of the tested sample that is mechanically tested—as opposed to the remainder of the sample—is thereby performed prior to, during and immediately after testing because drift and expansion in components thermally isolated from the test subject stage 110 are minimized Since the MEMS heater 100 is used in nanomechanical testing, the mechanical compliance of the MEMS heater 100 is critical in one example. The enhanced stiffness (in contrast to mechanical compliance) of the sample stage 52, including the MEMS heater 100, minimizes deflection of the sample stage and correspondingly minimizes false additional displacement measured by the probe 34 over the true actual penetration depth of the probe into the test sample 31. The stage plate 112 reinforces the stage subject surface 201 and enhances the stiffness of the sample stage 52. The material of the substrate 206 including the stage plate 112 is sufficiently stiff to not add its compliance to the mechanical data of the sample. For instance, the stage plate 112 and the substrate 206 include materials with high young's modulus, flexural modulus and the like, such as fused quartz or Zerodur. The stage plate 112 braces the stage subject surface 201 to substantially minimize deflection of the surface 201, for instance, during mechanical testing and observation. In another example, the support columns 203, 205 underlie and brace the stage subject surface 201 to enhance the stiffness of the stage subject surface. In contrast to the stiffness (the minimal mechanical compliance) of the MEMS heater 100, other heaters use membrane structures with enhanced mechanical compliance that permit mechanical deflection of the membranes and preclude use of the heaters for accurate mechanical testing. Optionally, the stage plate 112 is an integral part of the sample stage 52. For instance, the stage plate 112 and the test subject stage 110 (including the stage subject surface 201) are formed as a single piece of the sample stage 52 with the MEMS heater 100 disposed thereon. In another option, the stage plate 112 is coupled to the sample stage 52 to supplement the stiffness of the test subject stage 110 and the stage subject surface 201.

One of the important applications of the MEMS heater is electron microscopy in-situ nano-mechanical testing. Since electron microscopy uses a vacuum environment, the MEMS heater should be made of vacuum compatible materials which do not outgas in vacuum.

Fused quartz is an example of materials having low thermal expansion, low thermal conductivity, and low mechanical compliance with no out gassing in high vacuum. Fused quartz has coefficient of thermal expansion of 4.0 μm/m·K, thermal conductivity of 1.38 W/m·K, and young's modulus of 69 GPa. Those thermal and mechanical properties can provide satisfactory performance as the substrate 206 material.

The four holes 220, 222, 224 and 226 are designed for mechanical and electrical integration of the MEMS heater 100 with the base portion 54 of the test subject holder 55. The holes 220, 222, 224 and 226 are sized and shaped for receipt of conductive fixtures (eg. conductive screws) to mechanically fix the MEMS heater 100 to the base portion 54 of the test subject holder 55. The conductive fixtures also can make electrical connections by contacting heater and sensor leads 212, 214, 216 and 218 and the connectors on the base portion 54 of the test subject holder 55. The mechanical and electrical connections as described above are useful for TEM in-situ nanomechanical testing where minimal space is available for connection.

Since electron microscopy uses an electron beam for imaging, the test sample 31 accumulates the electrons if electrically isolated. An electron charged test sample 31 causes electrostatic force between a probe 34 and the test sample 31 and may cause a jump-to-contact as the probe 34 approaches the test sample 31. This electrostatic attraction by the accumulated electrons is undesirable for applications, such as indentation, because it distorts the measurement data, for instance the indentation loading/unloading curve. Discharging the electrons in the test sample 31 by electrically grounding the test sample improves the quantitative accuracy of mechanical measurements in electron microscopy in-situ mechanical testing.

Figure 3:
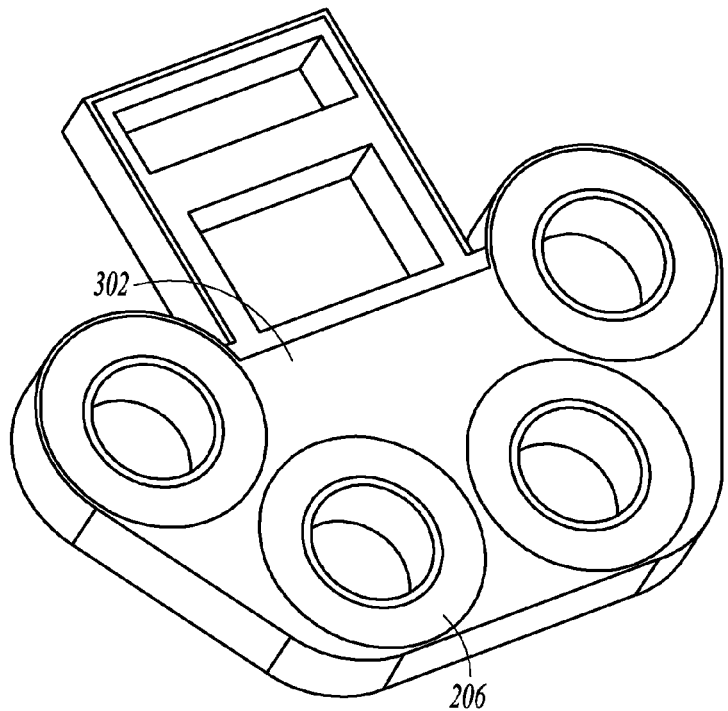
FIG. 3 is another perspective view showing a bottom view of the sample stage shown in FIG. 2A.

Referring now to FIG. 3, for discharging purpose, the bottom side of the MEMS heater 100 has a conductive thin film (e.g., metal or ceramic thin film) pattern 302. This conductive thin film 302 layer discharges electrons on the sample 31 (See FIG. 1). The conductive thin film 302 is electrically coupled with the test sample 31 by applying a conductive adhesive, epoxy, or paste between the test sample 31 and the conductive thin film 302. The conductive thin film 302 is electrically coupled with an electron microscopy ground to prevent any charge accumulation and electrostatic attraction between the test sample 31 and the probe 34 because of differing electrical potential.

Figure 4:
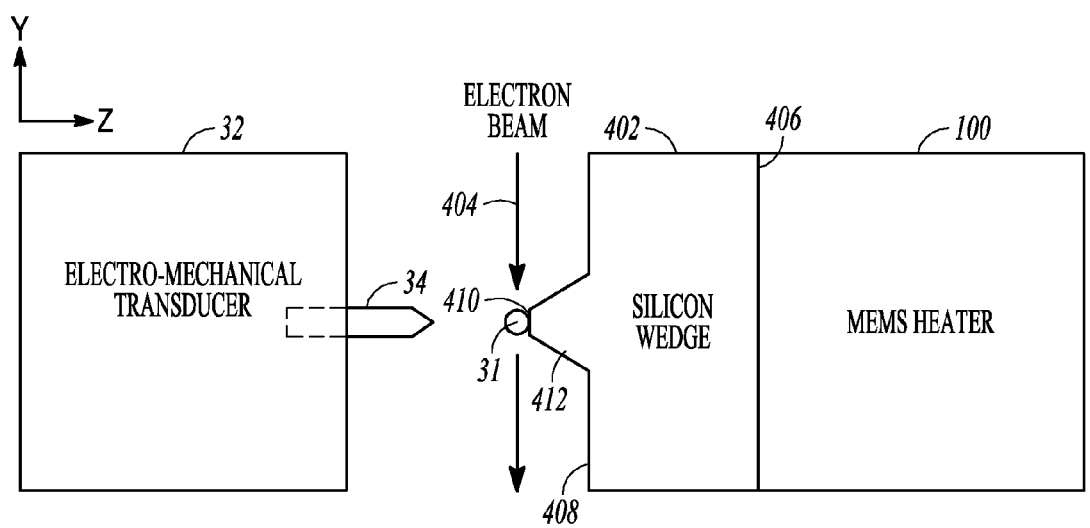
FIG. 4 is a schematic diagram of another example of a sample stage with a test sample positioned on a sample mount for mechanical testing and imaging.

The test sample 31 is mounted directly on the stage subject surface 201 of the MEMS heater 100, in one example. As shown in FIG. 4, for TEM in-situ nanomechanical testing, the test sample 31 is exposed to the electron beam and the beam is transmitted through the test sample 31. To make a thin test sample 31 along the electron beam 404 direction, the sample is deposited or attached on a sharp wedge-shaped sample mount 402 as shown in FIG. 4. The sample mount 402 includes a first side 408 including a sharp edge 410 along the wedge shape 412 for reception of the sample 31. A MEMS fabrication process is used to make the micro or nano scale sharp edge 410. The MEMS fabrication process includes, but is not limited to, deposition processes, focused ion beam lithography and milling, laser machining, photolithography and etching (dry or wet) and the like. With the configuration shown in FIG. 4, the test sample 31 and sample mount 402 are heated to the desired temperature using the MEMS heater 100. After the test sample reaches the desired temperature, the EM transducer 32 (See FIG. 1) actuates the displaceable probe 34 to test the sample 31. In one example, while the probe 34 indents the test sample 31, the mechanical data and the sample image are recorded simultaneously in real time by the displacement sensor 38 and the imaging device 96, respectively.

Because the stage subject surface 201 is parallel to the electron beam and positions the sample 31 on the sample mount 402 within the beam, electron transparency is maintained through the sample 31. Stated another way, the stage subject surface 201 and the sample mount 402 are positioned outside of the electron beam and do not underlie the beam emitter. The electron beam is thereby able to pass through the sample without distortion from underlying materials. Further, the sample stage 52 is braced by the stage plate 112 (described above and shown in FIGS. 2A, B). The stage plate 112 underlies the stage subject surface 201 and is also outside of the electron beam. Transparency of the sample 31 is thereby maintained while also providing a rigid test subject stage 110 with a stage subject surface 110. Stated another way, transmission electron microscopy is effectively performed on the sample 31 while at the same time mechanical testing (indentation, fracture, tension and the like) is permitted with negligible deformation of the underlying stage subject surface 201.

Figure 5:
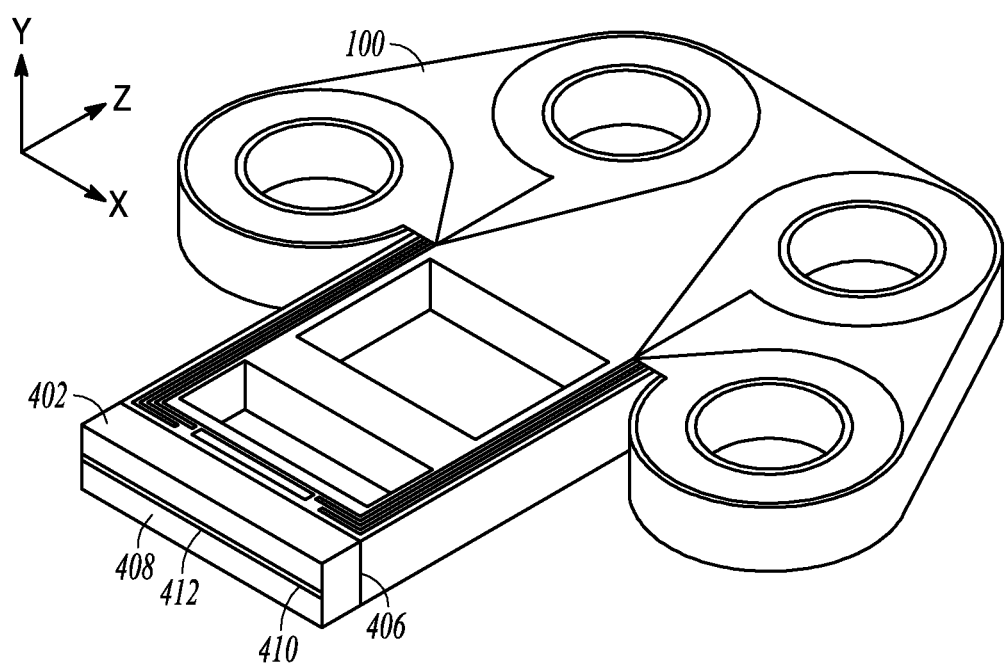
FIG. 5 is a perspective view of another example of a sample stage including a sample mount.

Referring to FIGS. 4 and 5, a second side 406 of the sample mount 402 is usually planar and perpendicular to the Z-axis. The planar second side 406 is coupled with the stage subject surface 201 of the MEMS heater 100. The front wall is similarly flat and perpendicular to the Z-axis for a flush coupling. An example of a sample mount 402 including a MEMS fabricated silicon wedge 412 having an edge 410 for mounting of a sample is shown in FIG. 5. The sample mount 402 has a wedge structure 412 fabricated on one side 408 of a silicon wafer. The planar second side 406 is on the other side of the mount 402 (e.g., a silicon wafer). Use of a heavily doped silicon wafer for the sample mount 402 fabrication makes the sample mount 402 conductive. By connecting the silicon mount 402 to the TEM ground, electrons on the test sample 31 are discharged to substantially prevent electrostatic attraction during imaging.

To evaluate the performance of the MEMS heater 100, finite element analysis (FEA) was performed using the commercially available finite element analysis software COSMOSWorks®. For the simulation, a model of the PicoIndenter 600 for the Hitachi TEM model H 800 and HF 2000 was used. FIGS. 6A, B show the model of the PicoIndenter including the test subject holder 55, the silicon wedge 402, the MEMS heater 100 and its coupling using fasteners 608, 610, 612 and 614 (e.g., brass screws). 158,989 triangular elements were generated for this simulation. Exemplary components of the tested MEMS heater 100, the test subject holder 55 and the other components shown in FIG. 6 are described herein. The silicon wedge 402 has a thermal conductivity of 124 W/m·K, a specific heat of 750 J/kg·K and a mass density of 2330 kg/m$^3$. A fused quartz material is used in the substrate 206 of the sample stage 52 and has a thermal conductivity of 1.38 W/m·K, a specific heat of 770 J/kg·K and a mass density of 2458 kg/m$^3$. The fasteners 608, 610, 612 and 614 are brass screws and have a thermal conductivity of 130 W/m·K, a specific heat of 420 J/kg·K and a mass density 8,260 kg/m$^3$. For the PicoIndenter 600, a titanium outer tube 620 is specified having a thermal conductivity of 22 W/m·K, a specific heat of 460 J/kg·K and a mass density of 4600 kg/m$^3$. The front end 606 of the test subject holder 55 includes a co-fired ceramic having a thermal conductivity of 46 W/m·K, a specific heat of 753 J/kg·K and a mass density of 3960 kg/m$^3$. The ball tip 604 is constructed with sapphire and has a thermal conductivity of 23 W/m·K, a specific heat of 761 J/kg·K and a mass density of 3980 kg/m$^3$. Thermal conductivity generally decreases and the specific heat generally increases as the material temperature rises. For evaluation purposes those properties are assumed constant. Steady state analysis and transient analysis were performed to investigate the temperature distribution, heating time and heating power.

Figure 7:
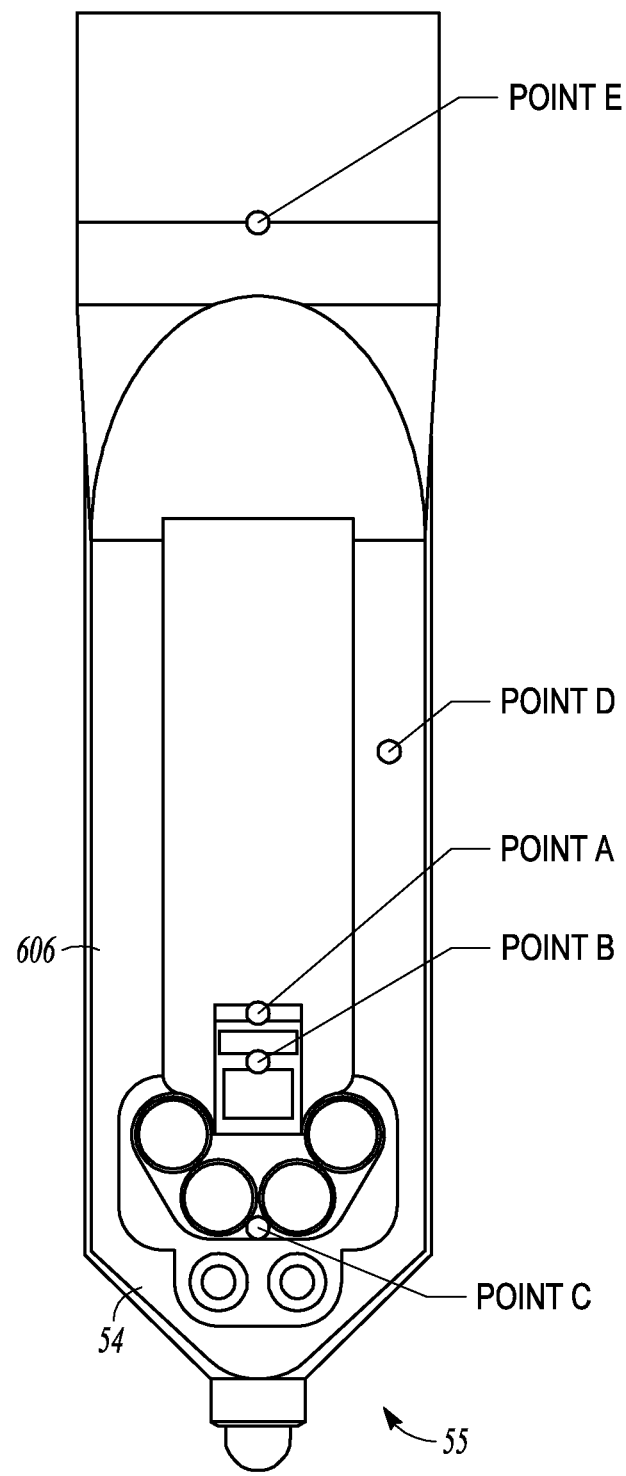
FIG. 7 is a detailed side view of another example of a test subject holder with points of interest marked.

For the steady state analysis, as boundary conditions, the heating element 202 was assumed to maintain a temperature of 420° C. and the outer tube surface with the largest diameter 602 and sapphire ball surface 604. were assumed to maintain a temperature of 20° C. The outer tube surface 602 with the largest diameter is the portion of the PicoIndenter holder 55 that makes contact with the TEM main body and heat transfers through this contact from the PicoIndenter to the TEM main body. FIG. 7 shows points of interest examined for both analyses (steady state and transient). At steady state, the estimated temperature at Point A (the stage subject surface 201) was 398° C., at Point B (between the base interface 53 and the front wall 201) it was 210° C., at Point C (the base interface 53) it was 21.7° C., at Point D it was 21.6° C., and Point E it was 21.5° C. There was a large temperature drop from the heating element 202 to the front end 606 of the PicoIndenter holder 55 including the holder base 54. As described above, the substantial temperature drop is desirable to minimize heating power needed to achieve a specified sample temperature with less thermal drift. As shown with the estimated temperatures, most of the temperature drop occurred at the fused quartz substrate 206 of the sample stage 52 indicating a minimal amount of heat transfer to the other components of the test subject holder 55 (e.g., larger components, such as the base portion 54 with corresponding larger thermal drift if heated). This result indicates that the same calibration constant of the sample stage 52 with the MEMS heater 100 can be used for different PicoIndenter holders. Stated another way, because substantially all of the heat generated within the sample stage 52 at the heating element 202 (See FIGS. 2A, B) is retained within the sample stage (i.e., not transmitted to the holder of the PicoIndenter), the sample stage is adaptable for coupling with different PicoIndenters without separate individual calibrations.

Figure 8:
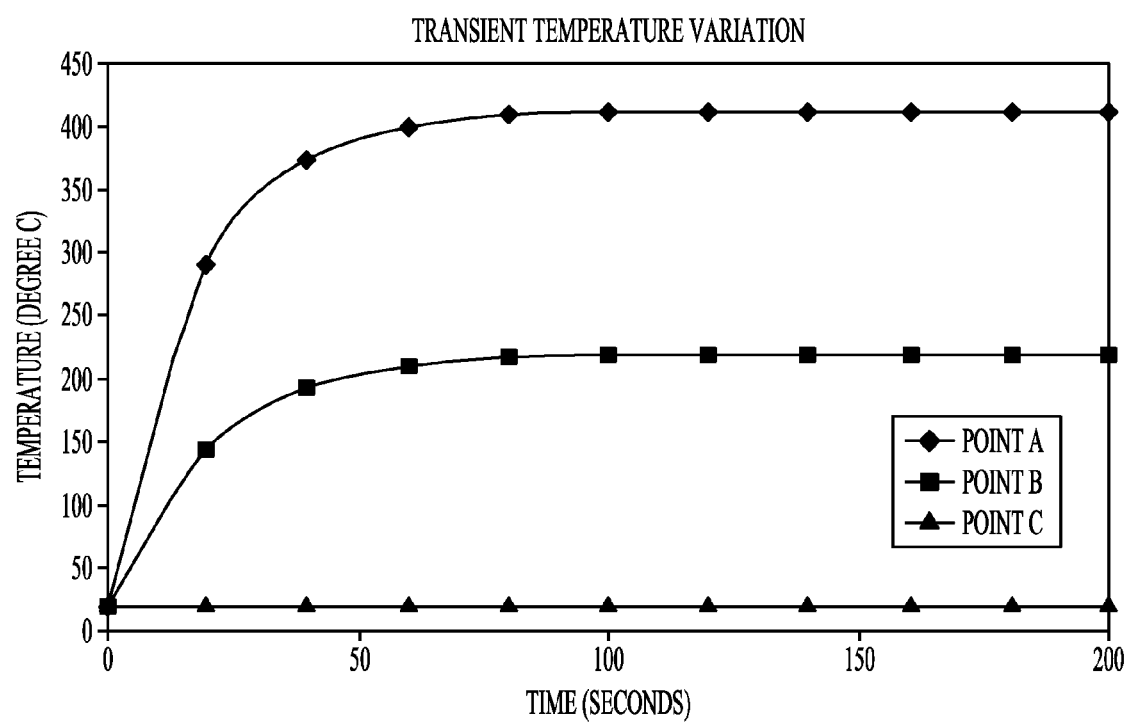
FIG. 8 is a graph showing temperatures at points A, B and C of FIG. 7 over time.

For transient thermal analysis, as boundary conditions, the heating element 202 is heated with 53 mW and the outer tube surface with the largest diameter 602 and sapphire ball surface 604 as shown in FIG. 6. were assumed to have a convection coefficient of 100 W/m$^2$·K. The larger convection coefficient is employed to model fast heat transfer through the outer tube and the sapphire ball 604. All the components are assumed to have a 20° C. temperature at the initially. Transient analysis was done over 200 seconds of heating at 20 second increments for points A, B and C (See FIG. 7). FIG. 8 shows the estimated temperature variation through the 200 second period. After a steep temperature rise for points A and B during the first 20 seconds, heat transfer slows. After 90 seconds of heating, the temperatures at points A and B are stabilized. Advantageously, because the MEMS heater 100 has an integrated temperature sensor (senor element 204), heating of the sample stage 52 is rapid, quantitative and accurate with a closed loop control scheme. In contrast, other methods associate a particular voltage with a temperature observed with an optical device, and use the observed relationship as a generalized calibration that is less accurate and subject to differences caused by a variety of factors (the sample material, differences in mass and volume of the stage and sample heated from those used for calibration, and the like).

Additionally, with the closed loop scheme and the integrated sensor 204, higher heating power is initially used while raising the test sample 31 temperature and lower heating power is gradually used as the test sample 31 temperature approaches the desired temperature (e.g., 420° C.). Although the testing data here includes a desired temperature of 420° C., the sample stage 52 including the MEMS heater 100 is configured, in one example, for heating to at least 1100° C. or more.

A sample stage 52 including the MEMS heater 100 was fabricated using metal deposition techniques and laser machining. As substrate 206 material, fused quartz is chosen. Fused quartz has a 1.38 W/m·K thermal conductivity which is about 100 times lower than that of silicon. The fused quartz also has low coefficient of thermal expansion (4.0 um/m·K) which helps to reduce the thermal expansion and drift during heating with the MEMS heater 100. The high young's modulus (i.e., stiffness) of fused quartz minimizes compliance to the applied force used for mechanical test and thereby mitigates the inclusion of deflection of the sample stage in displacement measurements and force calculations. The structural dimensions are determined based on the MEMS fabrication capability. The heating element 202 and sensing element 204 include platinum materials. Platinum is used up to 600° C. without degradation and has a linear temperature-resistance relation. As the heating element 202, a platinum thin film is deposited on 20-nm thick titanium adhesive layer. The dimension of the heating element 202 is 1.5 mm-long, 10-μm wide, and 0.15 μm thick. Considering the resistivity of platinum, 10.5 μΩ-cm, the resistance of the heating element was designed as 100Ω. With this resistance, the heating element has a much larger resistance than other resistance sources such as contact and lead resistances ensuring heating occurs at the heating element 202 and minimizing heating of the contacts and leads. The heater resistance also permits current flow resolution with 26 mA current flow to generate 70 mW the required heating power to raise the test sample 31 temperature to 400° C. A resistance value closer to the resistance value of the contacts and leads allows the contacts and leads to undesirably heat other portions of the sample stage 52. A higher resistance may decrease the temperature resolution because of a large heating power variation to the current flow resolution. For comparison, Hysitron's 400° C. heating stage manufactured for the TriboIndenter uses 750 mA current flow and 85 W heating power.

As the sensing element 204, a platinum thin film is deposited on a 20-nm thick titanium adhesive layer. The dimension of the sensing element 204 is 7.5 mm-long, 5-μm wide, and 0.15 μm thick. Considering the resistivity of platinum, the resistance of the sensing element 204 as described is 1,000Ω. The resistance of the sensor resistor is determined as 1,000Ω. As the nominal resistance increases, resistance variation to the temperature change also increases. Accordingly, making the resistance of temperature sensor 204 higher provides increased temperature sensing resolution. As the electrical leads from the heating and sensing elements to the sample stage, gold film is deposited on the titanium adhesive layer. FIGS. 6A, B show the fabricated sample stage 52 and MEMS heater 100 with the brass screw connections coupled with a test structure. The heating and sensing elements are electrically connected to the front end 606 using the gold leads patterned on the MEMS heater 100 of the sample stage 52 and the fasteners (e.g. four brass screws). The fasteners also mechanically fix the MEMS heater 100 and the sample stage 52 on the base portion 54.

Figure 9A:
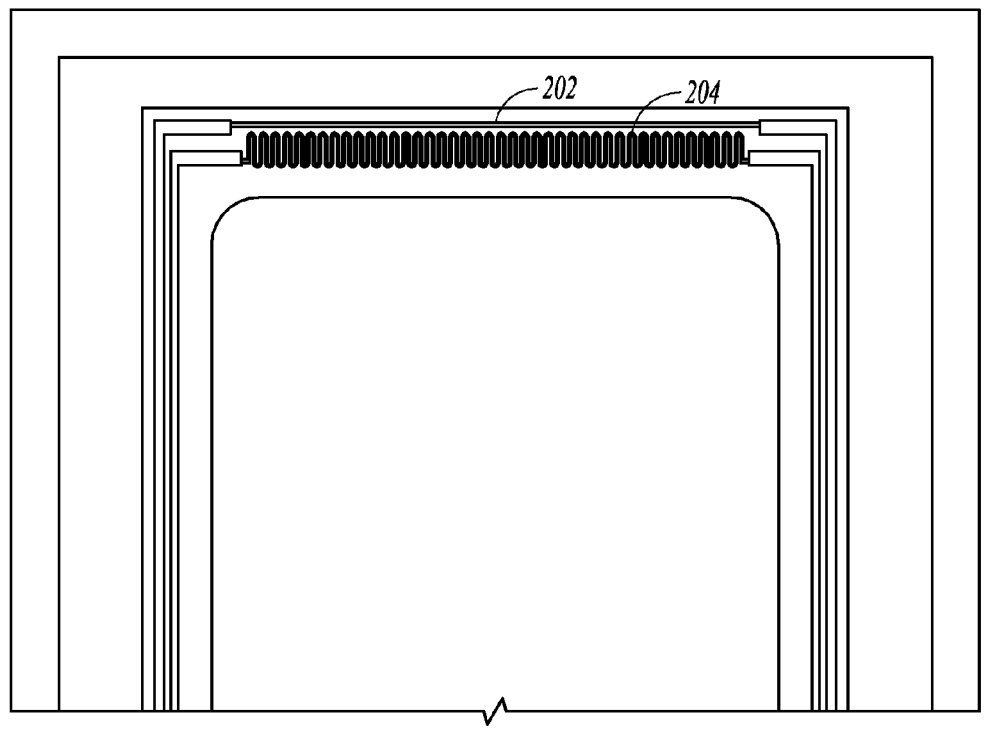
FIG. 9A is a top view of still another example of a sample stage at a microscopic scale.
Figure 9B:
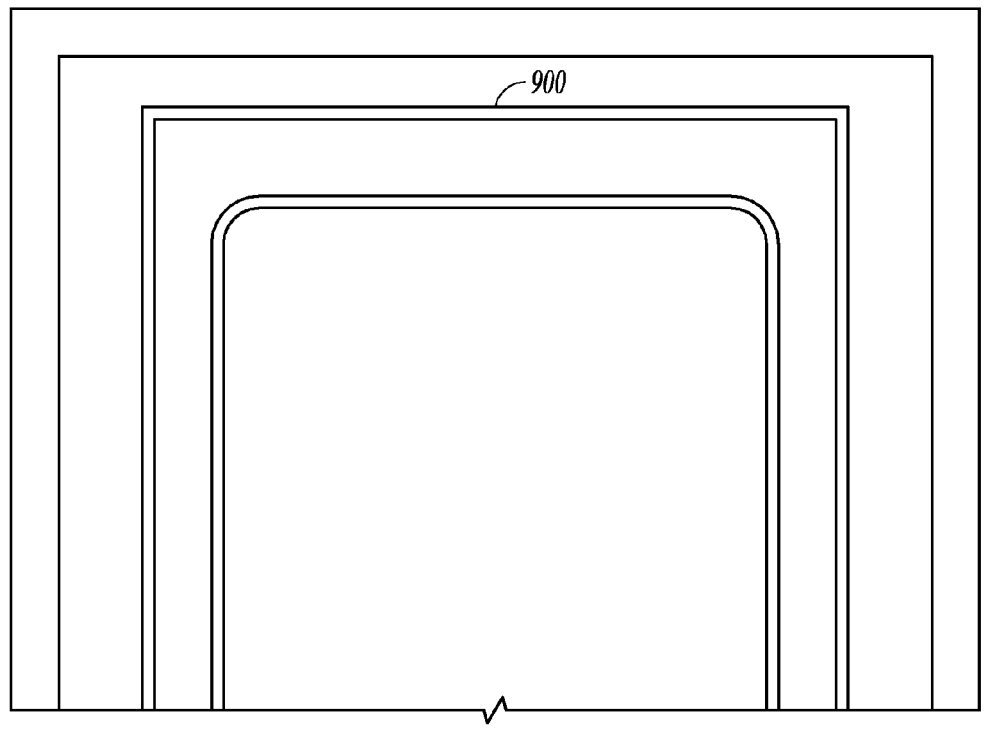
FIG. 9B is a bottom view of the sample stage shown in FIG. 9A at a microscopic scale.

Microscope images in FIGS. 9A, B show the top (FIG. 9A) and bottom (FIG. 9B) sides of the fabricated MEMS heater 100. The top side image shows the platinum heating and sensing elements and the gold leads patterns. The metallization is well done. However, there was resistance difference between the designed value and the measured value. The measured heater and sensor resistance at room temperature is about 250Ω and 2.5 kΩ respectively. Those values are about 2.5 times higher than the designed value. This difference does not make performance degradation since the driving electrical circuit can be adjusted for those resistances. Fabrication errors occur during micromachining fabrication processes. Such processes include, but are not limited to deposition processes, focused ion beam lithography and milling, laser machining, photolithography and etching (dry or wet). The front side of the MEMS heater wall is diced using a dicing saw to separate each individual heater from the fused quartz substrate wafer. Dicing creates a planar front side wall. The plane of the the front side wall is essential for consistently attaching a silicon wedge to the MEMS heater 100. The bottom side platinum lead 900 is patterned to discharge the electrons on the sample during the experiment inside TEM. This lead 900 connects the TEM ground and the silicon wedge 402. By discharging the electrons on the test sample 31, undesirable electrostatic interaction between the probe 34 and test sample 31 during the electron microscopy in-situ nanomechanical test is prevented.

Figure 12:
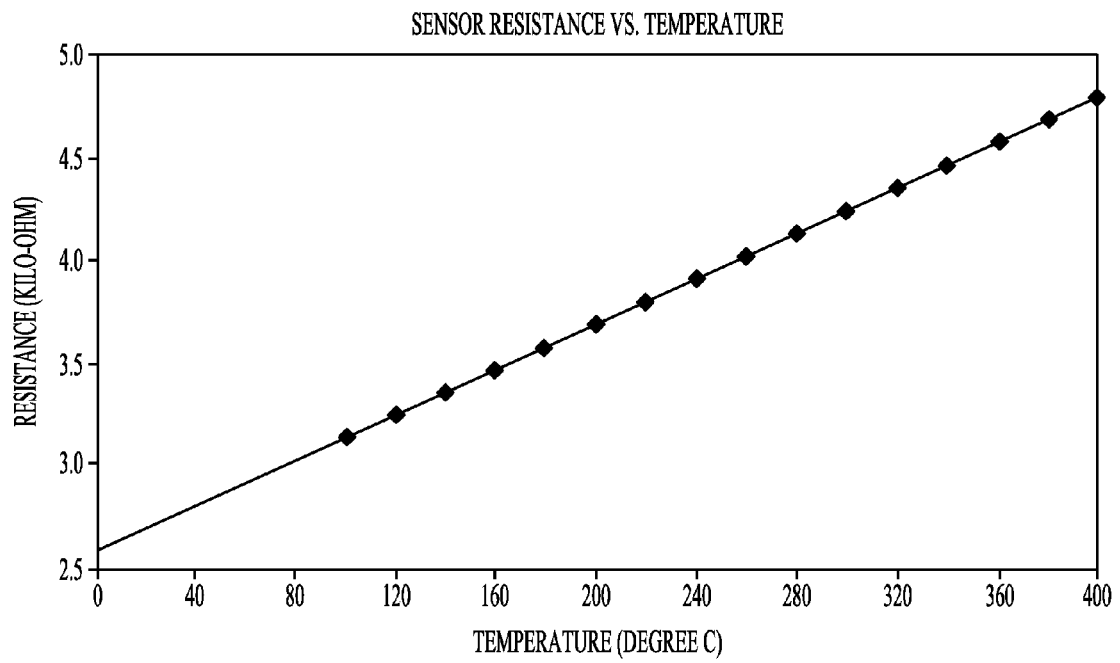
FIG. 12 is a graph showing resistance measurements of one example of a sensing element at different temperatures where a MEMS heater is annealed.

The fabricated MEMS heater 100 was annealed at 450° C. for 30 minutes. This annealing process makes inter-metallic diffusion which changes the heater and sensor characteristics. By annealing the MEMS heater at the temperature higher than the operating temperature, the heating element 202 and sensing element 204 can maintain the same characteristics within the operation temperature range (room temperature to 400° C.). After the annealing, the sensing element 204 showed repeatable and linear temperature-resistance characteristic. FIG. 12 is the measured sensing element 204 resistance at different temperatures. Resistance of the sensing element 204 is measured from 100° C. to 400° C. with 20° C. interval. The resistance changes at 5.6Ω/° C. within the measured temperature range. From the measured data, the thermal coefficient of the sensing element 204 is estimated as $\alpha = 0.00217°$ $C.^{-1}$ which indicates 0.217% resistance change per 1° C. temperature change compared to the nominal resistance at 0° C.

Figure 10:
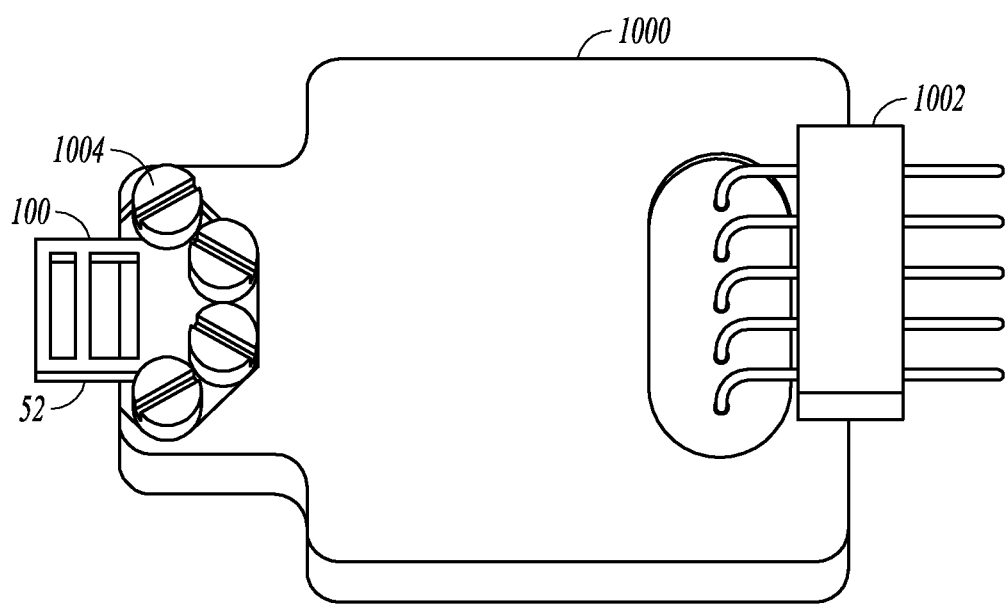
FIG. 10 is a perspective view of a sample stage including a MEMS heater coupled with an emulated indentation instrument component.

For testing purposes, the fabricated sample stage 52 including the MEMS heater 100 was integrated with the emulated PicoIndenter front end 1000 and heating circuit 1002 as shown in FIG. 10. The coupling by way of the fasteners does not mechanically damage the heater 100 and sample stage 52 and it secures electrical connections well. The contact resistance between the fasteners and the patterned gold lead (shown in FIG. 2B) is measured to be less than 0.5Ω. This low contact resistance is negligibly smaller than the heater and the sensor resistances. Because of the low contact resistance, the contact area between the front end 1000 and the sample stage 52 is not heated by current flow and does not thereby distort the sensor reading.

Figure 11:
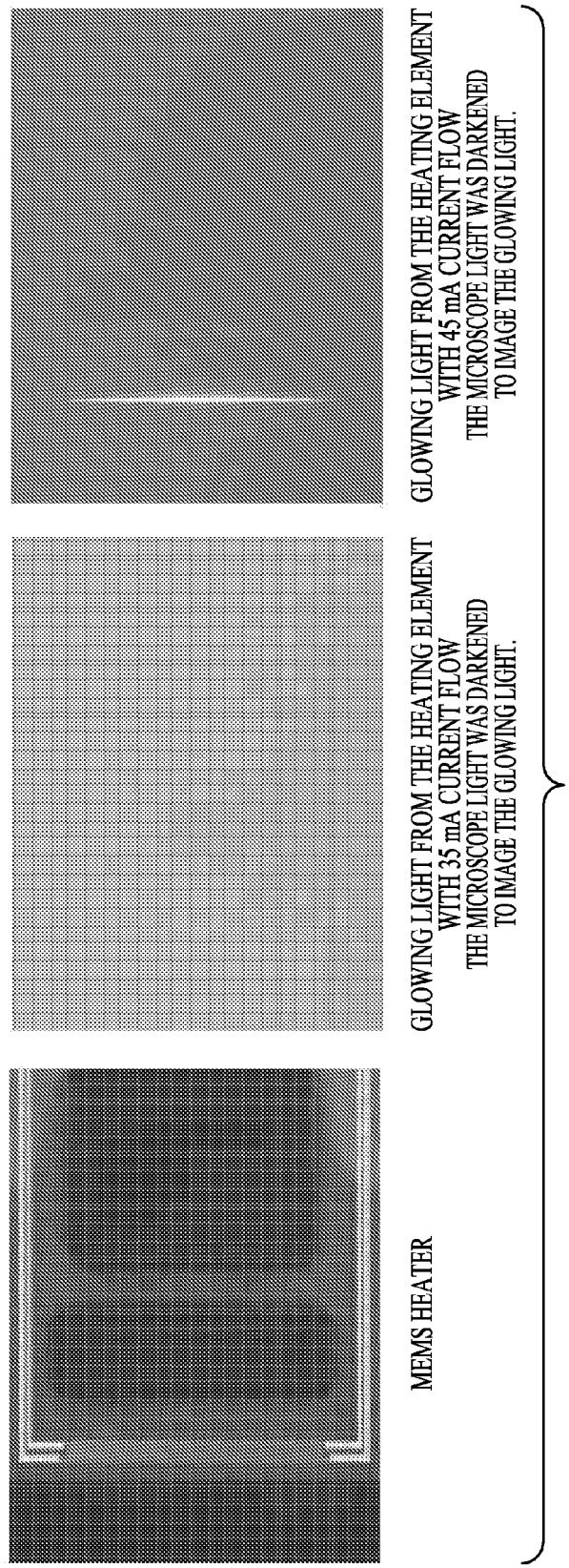
FIG. 11 shows a series of microscopic views of a sample stage with a MEMS heater with current applied to a resistive heating element.

FIG. 11 shows the heating experiment images under microscope. Current flow was applied on heater to check the heating element performance. The glowing light from the heater shows the heater is heated well above 600° C. and the glowing intensity change by heating power change shows that the heater is responding properly.

Figure 13:
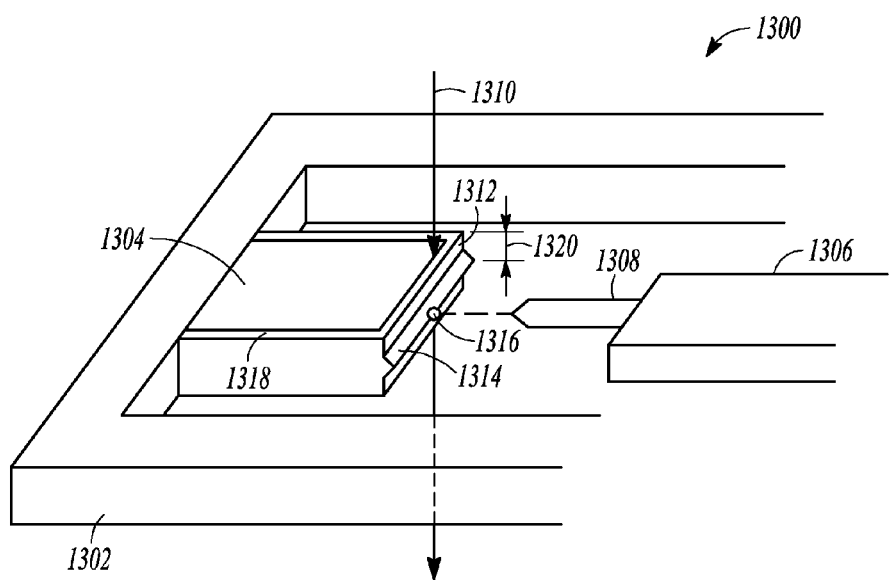
FIG. 13 is a schematic view of one example of a test subject holder with a sample stage including a MEMS heater.

FIG. 13 shows a schematic view of one example of a test subject holder 1300. The test subject holder 1300 includes a holder base 1302 coupled with a means for holding a test subject 1304. As described herein, in some examples, the means for holding the test subject 1304 includes a test subject stage including a sample stage and a base interface (See FIGS. 2A, B). The means for holding the test subject 1304 includes a subject surface 1312 configured to position a sample 1316 within an electron beam 1310 of a transmission electron microscope. As shown in FIG. 13, the subject surface 1312 includes a surface projection 1314, for instance a wedge shaped projection, that receives a sample 1316. When installed in the transmission electron microscope, the means for holding 1304 and the subject surface 1312 positions the sample within the electron beam 1310.

The test subject holder 1300 further includes a means for heating 1318. In one example, the means for heating 1318 includes a resistive MEMS heating element on the means for holding 1304. As previously described herein, the means for heating 1318 heats a portion of the means for holding 1304 (e.g., a test subject stage 110) and the sample 1316 to a specified temperature, for instance, 400 degrees Celsius or greater. The test subject holder 1300 with the means for heating are configured for use in ex-situ and in-situ heating and observation with optical, scanning probe and electron microscopes.

Also shown in FIG. 13 is an electro-mechanical transducer 1306 with a probe 1308. The electro-mechanical transducer 1306 performs mechanical testing and measurement of the sample 1316 on the subject surface 1312. For instance, the transducer 1306 performs indentation, tensile, compression, fracture, fatigue, tribology testing and the like.

As shown in FIG. 13, the means for heating 1318 is positioned adjacent to the subject surface 1312 and the sample 1316. Heating of the sample 1316 is thereby performed at the sample 1316 and not otherwise transmitted from a heating feature remote from the sample and the subject surface 1312. For instance, the means for heating 1318, such as a resistive heating element, is located adjacent to the sample 1316 according to an adjacent spacing 1320 of approximately 0.50 millimeters As previously described in other examples and discussed again here, the means for heating 1318 is configured to heat a portion of the means for holding of the test subject 1304. For example, the means for heating 1318 is configured to heat a minimal volume of the means for holding the test subject 1304 compared to the holder base 1302 and the remainder of the means for holding coupled with the holder base. By limiting the volume heated the means for heating 1318 is able to quickly heat the portion of the means for holding with the sample 1316 thereon and use less heating energy. By maintaining the means for heating 1318 adjacent to both the sample 1316 and the subject surface 1312 rapid heating with less energy expenditure is possible because there is minimal transmission of heat energy through other portions of the means for holding the test subject 1304. As described above, positioning the means for heating 1318 according to an adjacent spacing 1320 of around 0.50 millimeters locates the heating means 1318 adjacent (e.g., immediately adjacent) to the sample 1316 and the subject surface 1312. As further discussed below, the volume heated by the means for heating 1318 is in some examples limited by features such as voids, columns and a material of the means for holding a test subject 1304. These features alone or in combination cooperate with the placement of the means for heating adjacent to the subject surface 1312 to substantially limit the volume of the means for holding 1304 heated by the means for heating 1318.

As described in other examples herein, the means for holding a test subject 1304 includes in some examples voids, supports and thermally resistive materials configured to contain heat energy within a smaller volume of the means for holding a test subject 1304 relative to the remainder of the means for holding 1304 and the holder based 1302. These features and materials are described herein and are applicable to the means for holding 1304. Referring to the sample stage 52 in FIGS. 2A and 2B, for example, the support columns 203, 205 extending from the base interface 53 to the test subject stage 110 throttle heat transfer from a first portion of the sample stage 52 (e.g., a means for holding 1304) to the base interface 53. The support columns 203, 205 have a smaller cross sectional area along a plane parallel to the plane defined by the test subject stage 110. A smaller cross sectional area in the support columns 203, 205 relative to the test subject stage 110 throttles heat transfer from the test subject stage 110 toward the base interface 53 as well as the holder base 54 shown in FIG. 6B.

Additionally, one or more voids 208, 210 shown in FIGS. 2A and 2B, space the test subject stage 110 from the base interface 53 and the juncture between the base interface 53 and the holder base 54. Transmission of heat energy across the voids 208, 210 is difficult compared to conduction of heat energy through the material of the test subject holder 55. Additionally, in a vacuum (common in electron microscopes) transmission across the voids 208, 210 is only possible by minimal radiative heat transfer and not by relatively enhanced heat transfer through convection. The voids 208, 210 thereby throttle heat transfer from the test subject stage 110 to the remainder of the sample stage 52 including the base interface 53. The support columns 203, 205 (and the voids 208, 210 therebetween) position the test subject stage 110 (e.g., the subject surface 1312 including a sample 1316) remotely relative to the remainder of the sample stage 52 (means for holding a test subject 1304). The voids 208, 210 and support columns 203, 205 shown in FIGS. 2A, B thereby thermally isolate the subject surface 1312 (e.g., test subject stage) of the means for holding 1304 shown in FIG. 13 from the remainder of the means for holding and the test subject holder 1300.

While the test subject stage 110 (e.g., the subject surface 1312) is not completely thermally isolated from the remainder of the test subject holder 55 (e.g. holder 1300), heat transfer from the test subject stage 110 to the test subject holder 55 and base interface 53 is substantially minimized. For instance, in one example where a sample and the test subject stage 110 (e.g., sample 1316 and subject surface 1312) are heated to a temperature of around 400° C. or greater the remainder of the sample stage 52 adjacent to the holder base 54 is maintained at a temperature of around 50° C. or less.

Moreover, the means for holding a test subject 1304 is constructed with a thermally resistive material configured to resist conductive heat transfer from the subject surface 1312 to the holder base 1302 and a remainder of the means for holding 1304 (including for instance the base interface 53 as shown in FIG. 2A). For example, where the means for holding the test subject 1304 is constructed with fused quartz. Fused quartz has a coefficient of thermal expansion of around 4.0 μm/m·K and a thermal conductivity of around 1.38 w/m·K. With this minimal thermal conductivity the fused quartz substantially retards the transmission of heat from the subject surface 1312 to the holder base 1302. Further fused quartz experiences minimal thermal expansion at the heated subject surface 1312 because of its low coefficient of thermal expansion.

These features described immediately above and herein including the columns 203, 205, voids 208, 210 as well as the materials of the means for holding the test subject 1304 operate alone or together to thermally isolate and thereby substantially retard heat transfer from the subject surface 1312 to the remainder of the means for holding a test subject 1304 and the holder base 1302. These features either alone or in combination ensure that heating through the means for heating 1318 of the sample 1316 is substantially contained adjacent to the subject surface 1312 to provide rapid heating of the sample 1316 with relatively low amounts of heat energy. Stated another way, because of the thermal isolation of the subject surface 1312 and sample 1316, the means for heating 1318 substantially heats the subject surface 1312 and the sample 1316 while only minimally transmitting heat from the subject surface to the remainder of the means for holding 1304 (including for example, the base interface 53 and the holder base 55 shown in FIG. 6B).

Because heating of the subject surface 1312 is substantially localized at the subject surface and the sample 1316 with only minimal heat transferred to the remainder of the means for holding 1304, mechanical drift and thermal expansion of the material of the means for holding the test subject 1304 as well as the holder base 1302 are substantially minimized Mechanical drift and thermal expansion of the materials comprising the holder base 1302 and the means for holding the test subject 1304 are proportional to the dimensions and volume of the materials of each of those elements heated during operation of the means for heating 1318. Because the volume heated by the means for heating 1318 is substantially limited to the subject surface 1312 and the sample 1316 mechanical drift and thermal expansion are thereby minimized For example, with the minimal heat transfer through the support columns 203, 205 and across the voids 208, 210 along with the thermally resistive material of the means for holding, the remainder of the means for holding and the holder base 1302 experience minimal heating and thereby experience minimal mechanical drift and thermal expansion. In another example, the sample surface 1312 is constructed with a material, such as fused quartz, having a low coefficient of thermal expansion. Heating of the sample surface 1312 thereby results in minimal thermal expansion of the surface.

A portion of the sample 1316 observed, for instance, through transmission electron microscopy is thereby held substantially static during heating with the means for heating 1318. The sample 1316 including the portion observed, is further held statically for both mechanical testing with the electro-mechanical transducer 1306 and observation by the electron beam 1310 of a transmission electron microscope. That is to say, a portion of the sample 1316 at a micron or less scale (e.g., nano-scale) is observable by a transmission electron microscope during heating as well as mechanical deformation and testing and thereafter. Mechanical properties of the material making up the sample 1316 are thereby observable before heating, during heating, during mechanical testing and immediately thereafter by observation of one discrete portion of the sample throughout testing.

Additionally, as described herein, the means for holding a test subject 1304 in other examples includes a support, such as a stage plate 112 shown in FIG. 2A. The support braces the subject surface 1312 of the means for holding 1304. The support (e.g., the stage plate 112) braces the subject surface 1312 and the sample and minimizes deflection of the subject surface during mechanical testing with the electro-mechanical transducer 1306. Observation of the sample 1316 and accurate assessment of the sample properties are thereby possible through a transmission electron microscope without the distortion caused by deflection of the subject surface.

As described above, the subject surface 1312 with the support provides a robust surface for positioning and observation of the sample 1316. Because the sample 1316 is positioned on the subject surface 1312 and because the surface is positioned outside of the electron beam 1310 electron transparency is maintained through the sample 1316 thereby providing distortion free observation of the sample 1316. Stated another way, the subject surface 1312 supports the sample 1316 during mechanical testing with the electro-mechanical transducer 1306 and minimizes deflection of the surface and the sample while also maintaining electron transparency of the sample 1316 (e.g., because the electron opaque subject surface 1312 is positioned outside of the electron beam 1310). For instance, as shown in FIG. 13, the subject surface 1312 is oriented parallel to the electron beam 1310 with the surface projection 1314 presenting the sample 1316 and extending toward the electron beam 1310. Because the sample 1316 is provided along the edge of the surface projection 1314 the sample itself as opposed to the (electron opaque) subject surface 1312 is positioned within the electron beam 1310 to maintain electron transparency.

In contrast, in some examples sample stages provide deflectable membranes and wires underlying the sample. These features, such as wires and membranes, allow for electron transparency but they are not sufficiently robust to brace against deflection from mechanical testing, such as nano-indentation. In other examples, where a sample is positioned on a robust surface capable of providing support against mechanical testing, electron transparency is not maintained because the support is positioned within the electron beam axis. The means for holding a test subject 1304 described herein addresses both of these issues by providing a robust support in the subject surface 1312 (e.g., a stage plate 112) as well as an electron transparent sample 1316 through positioning of the subject surface 1312 outside of the electron beam 1310.

Figure 14A:
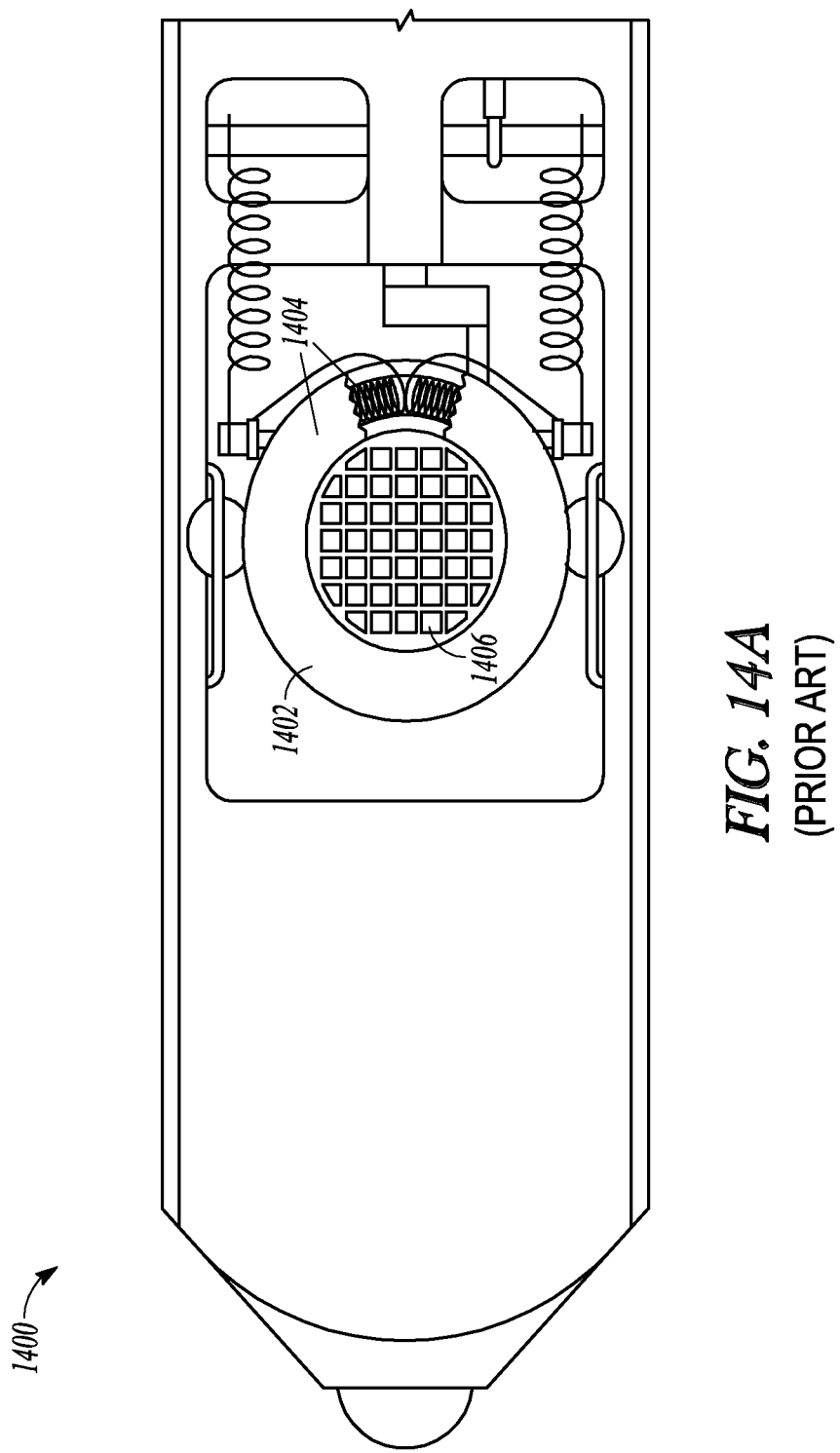
FIG. 14A is a prior art figure showing one example of a specimen cradle including a specimen membrane.
Figure 14B:
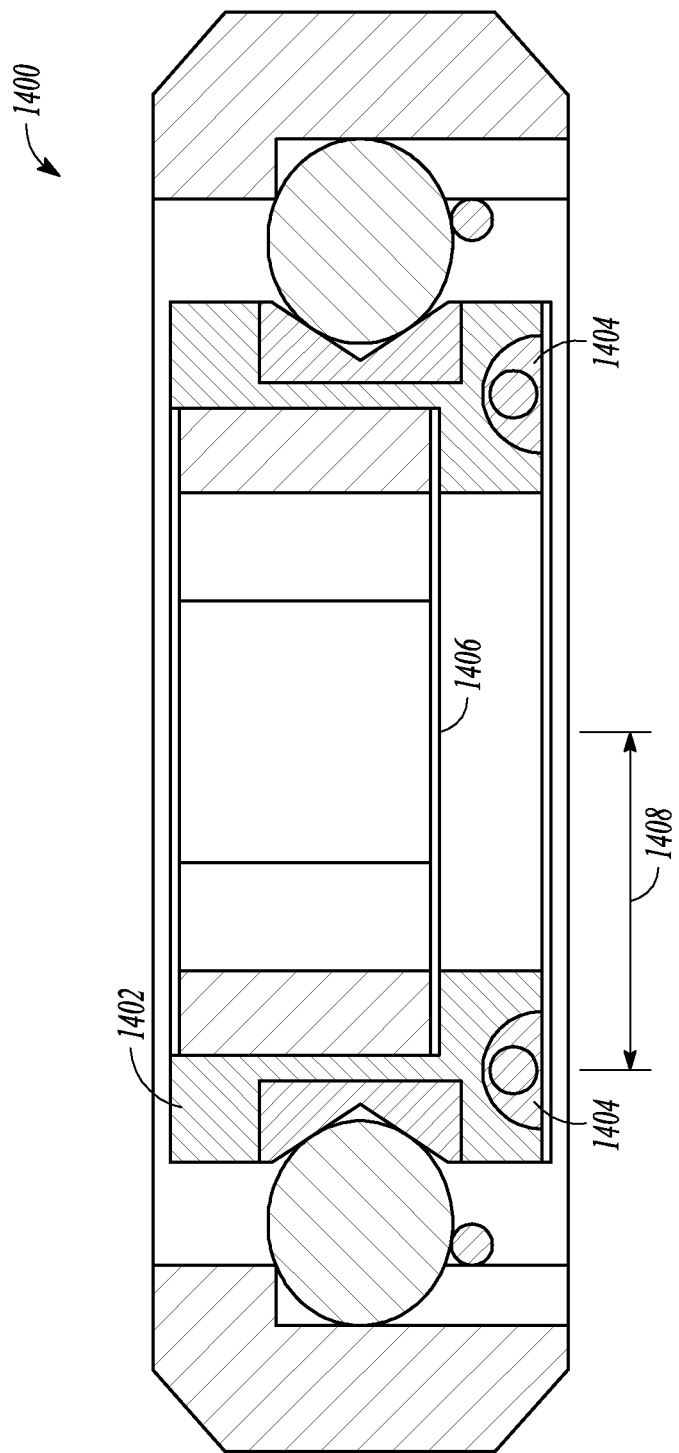
FIG. 14B is a cross-sectional view of the specimen cradle shown in FIG. 14A.

Referring now to FIGS. 14A and 14B, one example of a prior art test subject holder 1400 is shown. The test subject holder 1400 includes a specimen cradle 1402 movably positioned within the test subject holder. The specimen cradle 1402 includes a specimen area 1406 configured to receive a specimen for observation under a transmission electron microscope. The specimen area 1406 is surrounded by a heating element 1404 configured to heat the specimen area 1406 and the specimen. In the example shown, the heating element 1404 includes a heating element extending through the periphery of the specimen cradle 1402 and substantially surrounding the specimen area 1406.

Referring now to FIG. 14B, the test subject holder 1400 including the specimen cradle 1402 is shown in a cross sectional view. The heating element 1404 extends into and out of the page and around the periphery of the specimen cradle 1402 to surround the specimen area 1406. As shown in FIG. 14B, the specimen area 1406 is remotely spaced according to a remote spacing 1408 from the heating element 1404. In one example, the heating element 1404 is positioned away from the specimen area 1406 around 1.5 millimeters. The heating element is positioned away from the specimen area 1406 (e.g., a membrane) to maintain electron transparency through the specimen area 1406. Stated another way, the heating element 1404 is positioned peripherally away from the specimen area 1406 to allow observation of a specimen on the specimen area 1406 through transmission electron microscopy. Because the heating element 1404 is positioned remotely relative to the specimen area 1406 a significant amount of heat energy is needed to heat the specimen area 1406 to a specified temperature. Further, because the heating element 1404 is positioned within the specimen cradle 1402 surrounding the specimen area 1406 heating of the heating element 1404 not only must heat the specimen area 1406 it must also heat the remainder of the specimen cradle 1402 to achieve the specified temperature on the specimen area 1406.

In one example, the heated volume of the specimen cradle 1402 in the specimen area 1406 is greater than a volume of the test subject stage 110 shown in FIGS. 2A, 2B. Because the specimen area 1406 is not thermally isolated from the specimen cradle 1402 heat energy from the heating element 1404 is transmitted within the specimen cradle 1402 as well as the specimen area 1406. In some examples, it thereby requires additional heat energy and time to heat the specimen area 1406 to a specified temperature. Further it requires additional heat energy to maintain the specimen area 1406 at the desired temperature.

In contrast to the test subject holder 1400 shown in FIG. 14A, 14B, the test subject holder 1300 shown in FIG. 13 includes the subject surface 1312 having the means for heating 1318, such as a heating element, positioned adjacent to the subject surface and sample 1316. As previously described, for example, the means for heating 1318 is positioned adjacently according to an adjacent spacing 1320 to the sample 1316. For instance, the adjacent spacing 1320 is around 0.50 millimeters compared to the remote spacing in the example shown in FIG. 14B of around 1.5 millimeters. At a micron or nanoscale the difference in spacing between the sample and the heating element in the test subject holders 1300 and 1400 provides significant differences in the amount of heat energy needed to elevate the temperature of a sample to high specified temperatures. Stated another way, the adjacent spacing 1320 positions the means for heating 1318 immediately adjacent to the sample 1316 (with the above described heating benefits) when compared to the remote spacing 1408 of the specimen cradle 1402.

Furthermore, because there is a difference in the spacing of the heating elements relative to the samples the volume of the specimen cradle 1402 heated by the heating element 1404 is much greater than the volume of the subject surface 1312 heated by the means for heating 1318. In one example, the heated volume of the specimen cradle 1402 is exponentially larger (e.g., an exponent of 3) because of the cubed relationship of dimensions such as radius, depth, and circumference to volume. Stated another way, where the remote spacing 1408 of the specimen cradle 1402 is greater than the adjacent spacing 1320 of the means for heating 1318 relative to the sample 1316 the heated volume of the specimen cradle 1402 is exponentially larger than that of the means for holding the test subject 1304 thereby requiring additional heat energy to achieve and maintain a specified temperature of a sample.

In one example, because of the remote spacing 1408 of the heating element 1404 from the specimen area 1406 and the corresponding greater volume of the specimen cradle 1402, mechanical drift and thermal expansion of the specimen cradle 1402 is greater than corresponding drift and expansion in the means for holding the test subject 1304 shown in FIG. 13 as well as the other examples of sample stages shown herein. As previously described, heating a larger volume of material correspondingly produces greater mechanical drift and thermal expansion relative to heating of a smaller volume, such as a volume of material equivalent to the test subject stage 110 shown in FIG. 2A and the subject surface 1312 shown in FIG. 13. By thermally isolating the subject surface 1312 relative to the remainder of the sample stage as well as the holder base 1302 with the features described herein (e.g., support columns, voids thermally resistive materials and the like) corresponding mechanical drift and thermal expansion are minimized. Stated another way, because the holder base 1302 and the remainder of the means for holding the test subject 1304, (e.g., the base interface 53), are thermally isolated only a small fraction of the heat within the subject surface 1312 (test subject stage 110) is transmitted into those features.

As previously described, holder base 1302 and the remainder of the means for holding 1304 (e.g., base interface 53) have a larger volume relative to the subject surface 1312 and the sample 1316. Because this large volume is not substantially heated due to the thermal isolation mechanical drift and thermal expansion of these features is minimized In contrast, the specimen cradle 1402 shown in FIGS. 14A, B includes the heating element 1404 in the ring surrounding the specimen area 1406. Heating of the specimen area 1406 correspondingly heats the entirety of the specimen cradle 1402 and causes mechanical drift and thermal expansion throughout the specimen cradle 1402. As previously described, mechanical drift and thermal expansion of the test subject holder such as test subject holder 1400 moves the sample including a discrete portion of a sample observed through transmission electron microscopy. Because in some examples, the specimen cradle 1402 fails to minimize the mechanical drift and thermal expansion of the cradle, consistent observation of a discrete portion of the specimen area 1406 is difficult.

Referring again to FIGS. 14A and 14B, the specimen area 1406 extends across the specimen cradle 1402. The specimen area 1406 is electron transparent to permit the transmission of electrons through the specimen area including the sample for observation during transmission electron microscopy. Because the specimen area 1406 is transparent the specimen area 1406 is capable of deflection when subjected to mechanical testing such as fatigue, indentation, tensile, fracture testing and the like. Observation of mechanical properties of the sample on the specimen area 1406, for instance, at or near the time of mechanical testing through transmission of electron microscopy is thereby difficult as the mechanical properties of the sample are distorted through undesired deflection of the specimen area 1406. In contrast, the subject surface 1312 shown in FIG. 13 is positioned outside of the electron beam 1310 and positions the sample 1316 within the electron beam. A robust support, such as a stage plate 112 (shown in FIGS. 2A, 2B) braces the sample and the subject surface 1312 during mechanical testing, for example, testing with the electro-mechanical transducer 1306. Mechanical properties of the sample 1316 are readily observed throughout heating, mechanical testing and afterward as the electron beam is directed through the sample 1316 because of minimal deflection of the sample 1316 and minimized mechanical drift and thermal expansion.

Figure 15:
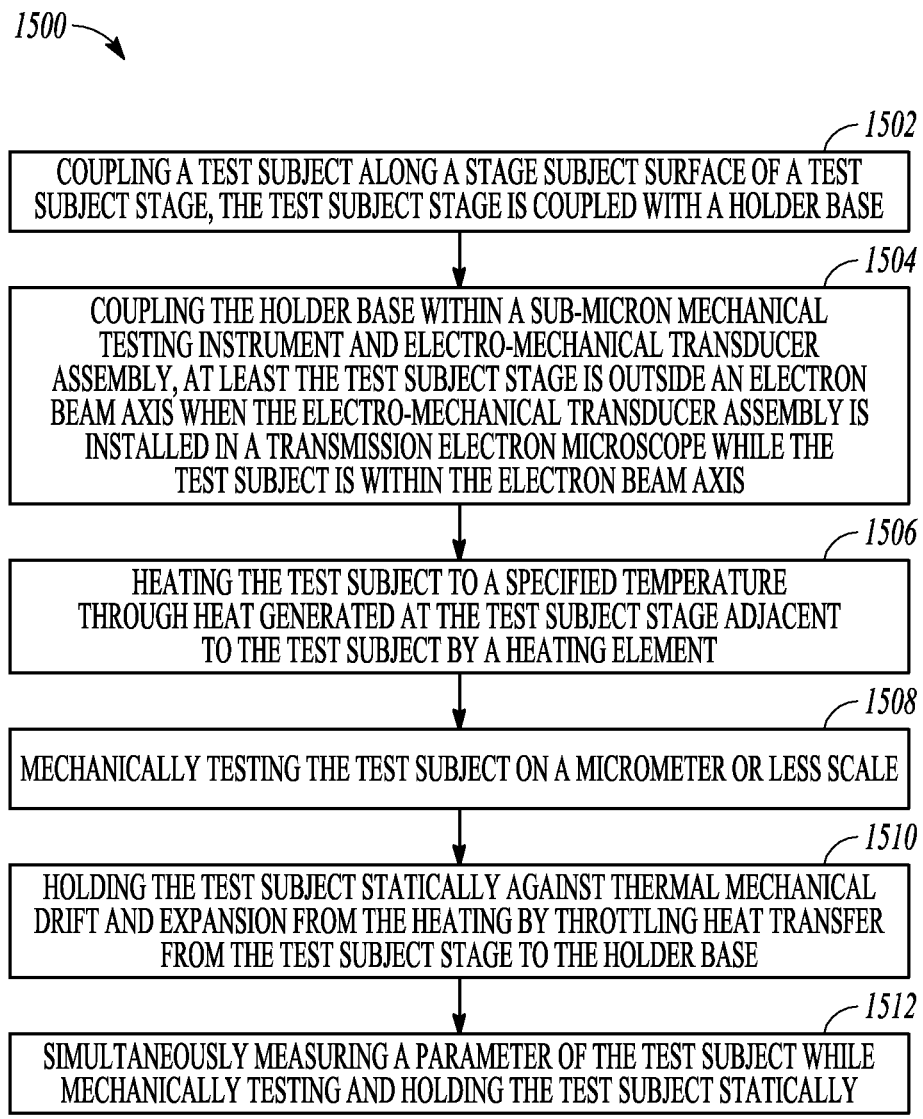
FIG. 15 is a block diagram showing one example of sub-micron heating and mechanical testing.

FIG. 15 shows one example of a method 1500 for submicron heating and mechanical testing of a test subject. Reference is made in the description of method 1500 to features and elements previously described herein. Where convenient, reference numerals previously described are included in the description of the method 1500. The references are not intended to be limiting. For instance, where a single reference numeral is provided it is also implied reference is made to all similar features as well as their equivalents.

At 1502, a test subject such as a sample is coupled along a stage subject surface 201 of a test subject stage 110. The test subject stage 110 is coupled with a holder base, such as holder base 54 shown in FIG. 6B. In one example, coupling of the test subject along the stage subject surface 201 includes mounting of a sample on a sample mount 402 as shown in FIGS. 4 and 5. The test subject stage 110 includes the stage subject surface 201 underlying the sample mount 402. In another example, the stage subject surface includes the first side 408, sharp edge 410 and wedge shape 412 of the sample mount 402. Stated another way, the sample mount 402 is included as a part of the test subject stage 110 and the stage subject surface 201.

At 1504, the holder base 54 is coupled within a submicron mechanical testing instrument and electro-mechanical transducer assembly, such as the electro-mechanical transducer 32 shown in FIG. 1. As shown in FIG. 4, the test subject stage, including the MEMS heater 100 and the sample mount 402 is positioned outside an electron beam axis 404 of the electro-mechanical transducer assembly 32 when installed in a transmission electron microscope. The test subject stage 110 positions a sample, such as a sample 31 shown in FIG. 4, within the electron beam (see beam 404 in FIG. 4). Stated another way, the MEMS heater 100 including the test subject stage 110 positions the sample 31 within the electron beam axis while the test subject stage 110 is positioned outside of the electron beam to provide electron transparency through the sample 31.

At 1506, the test subject is heated to a specified temperature through heat generated at the test subject stage 110 adjacent to the test subject with a heating element, such as heating element 202 shown in FIG. 2B. In one example, the heating element 202 is positioned immediately adjacent to the stage subject surface 201 of the test subject stage 110. That is to say, the heating element 202 is not remotely positioned relative to the stage subject surface, and heat transfer to the stage subject surface as well as the sample positioned on the stage subject surface is localized to the volume of the test subject stage 110 containing the stage subject surface 201. As previously described, by localizing the generation of heat to the area adjacent to the stage subject surface 201 mechanical drift and thermal expansion of materials of the remainder of the sample stage 52 and the holder base 54 are substantially minimized At 1508, the test subject is mechanically tested on a micron or less scale. Mechanical testing of the test subject includes, but is not limited to, testing with the electro-mechanical transducer 32. Mechanical testing with the electro-mechanical transducer 32 includes, but is not limited to, indentation, compression, tensile, fatigue, tribology, fracture testing and the like. As previously described herein, testing of a sample on the test subject stage 110 on the sample stage 52 is performed with little or no distortion due to deflection of the test subject stage 110 because of the stage plate 112 coupled along the test subject stage 110. In one example, the stage plate 112 is formed integrally with the test subject stage 110 and the sample stage 52. The stage plate braces the test subject stage 110 and the sample thereon against deflection caused by mechanical testing from the instruments on the electro-mechanical transducer 32. Observation of the test subject on the test subject stage 110 is thereby performed with minimal distortion from deflection of the test subject stage 110 compared to distortion caused by mechanical testing of samples on other substrates including membranes and wires. As discussed above, mechanical testing as described in 1508 is performed on a sample positioned within an electron beam axis that is electron transparency while still providing a robust test subject stage 110 capable of absorbing and minimizing deflection caused by the mechanical testing.

At 1510, the test subject (e.g., the sample 31 as shown in FIG. 4) is statically held against thermal mechanical drift and expansion from heating by throttling heat transfer from the test subject stage 110 to the holder base 54 as well as the base interface 53 of the sample stage. In one example, throttling of heat transfer includes throttling heat transfer out of the test subject stage 110 through one or more supports 203, 205 coupling the test subject stage with the remainder of the sample stage 52 and the holder base 54 (See FIGS. 2A, B). For instance, the one or more supports 203, 205 have a smaller cross-sectional area along a direction of heat transfer from the test subject stage 110 to the holder base 54 and the base interface 53. The cross-sectional area is smaller compared to a test subject stage cross-sectional area in the same direction. Stated another way, because the supports have a smaller cross-sectional area than the test subject stage 110 the supports 203, 205 effectively provide a narrow passage for conduction of heat into the remainder of the sample stage 52 and the holder base 54.

In another example, the test subject stage 110 has a first thermal resistance greater than a second thermal resistance of the holder base 54. That is to say, because the first thermal resistance of the test subject stage 110 and the sample stage 52 is greater than that of the holder base 54, heat transfer from the test subject stage 110 through the support columns 203, 205 as well as the base interface 53 is effectively retarded by the material prior to reaching the holder base 54.

In still another example, the sample stage 52 includes one or more voids 208, 210 as shown in FIG. 2A. The voids 208, 210 are formed between the support columns 203, 205 and provide gaps between the test subject stage 110 and the base interface 53 of the sample stage 52. Radiant heat transfer across the voids 208, 210 is minimal compared to conductive heat transfer. In the case where the atmosphere around the sample stage 52 and the holder base 54 is a vacuum (e.g., for instance during heating, testing and observation) the vacuum ensures that only radiant heat transfer across the voids is possible while conductive heat transfer through the support columns 203, 205 is minimized as described herein. Radiant heat transfer across the voids 208, 210 is minimal compared to the already small amount of heat transfer possible through the support columns 203, 205 and thermally isolates the test subject stage 110 from the remainder of the sample stage 52 and the holder base 54.

As discussed above, by throttling the heat transfer from the test subject stage 110 to the base interface 53 coupled with the holder base 54 mechanical drift and thermal expansion of features other than the test subject stage 110 and the sample 31 on the test subject stage 110 are minimal. For instance, where a heating element is positioned remotely relative to a specimen membrane heating of the heating element must also heat the volume of the specimen cradle surrounding the membrane as well as the membrane itself causing thermal expansion and mechanical drift of the specimen cradle and the membrane. In contrast, because the heating element 202 of the sample stage 52 is localized to the area adjacent to the test surface stage 110 and the sample on the stage subject surface 201 (e.g., immediately adjacent relative to the remote spacing of the heating element 1404 relative to the specimen membrane 1406 of the prior art shown in FIGS. 14A, 14B) drift and thermal expansion are minimized Heating of a small portion of the sample stage 52, such as the test subject stage 110, is performed without conesponding significant heating of the remainder of the sample stage 52 and the holder base 54. Throttling of heat transfer from the test subject stage 110 substantially minimizes the heating of these other components and thereby minimizes their conesponding thermal mechanical drift and expansion.

At 1512, a parameter of the test subject is simultaneously measured while mechanically testing and holding the test subject statically. Stated another way, because the sample stage 52 is capable of heating a sample on the test subject stage 110 with little or no thermal mechanical drift and thermal expansion as described above, mechanical testing is performed on the sample and the electron beam of a transmission electron microscope is able to observe the sample before, during and immediately after the testing. Simultaneous measurement of the parameter of the test subject includes observation and testing at substantially the same time as well as synchronously observing the test subject prior to mechanical testing, during testing and then immediately after mechanical testing. Because of the minimization of thermal mechanical drift and expansion due to the throttling of heat transfer from the test subject stage 110 a portion of the test sample, for instance, at a micron or nano-scale is observed throughout heating, testing and the time immediately after testing. Difficult to observe features as well as measurements of properties of the test sample 31 are thereby observable throughout the method 1500.

Several options for the method 1500 follow. In one example, the coupling of the test subject along the stage subject surface 201 includes mounting the test subject on the sample mount such as sample mount 402. Heating of the test subject includes equally distributing heat throughout the sample mount 402. For instance, where the sample mount 402 includes a material having a greater thermal conductivity than the sample stage 52 heat transferred into the sample mount 402 is readily transmitted throughout the sample mount to evenly heat the entire sample mount. In another example, the method 1500 includes sensing the temperature of the test subject stage 110 with a sensing element 204 positioned at the test subject stage. As shown in FIG. 2B, the sensing element 204 is positioned adjacent to the heating element 202 as well as the stage subject surface 201. Positioning of the sensing element 204 adjacent to these features enables the sensing element 204 to accurately determine the temperature of the test subject stage 110 throughout heating of the sample 31. In still example, the method 1500 includes controlling heating of the test subject with a closed or open loop control system including the heating element 202 and the sensing element 204 at the test subject stage 110.

In another example, heating the test subject to the specified temperature includes heating only a test subject stage 110 volume and the test subject. Stated another way, heat transfer is effectively throttled into the remainder of the sample stage 52 including the base interface 53 as well as the holder base 54. Corresponding heat transfer to the remainder of the sample stage 52 and the holder base 54 is thereby minimal with heating of the sample stage 52 limited to the test subject stage 110 volume as well as the test subject on the test subject stage 110. For instance, heating of only the test subject stage volume as well as the test subject includes maintaining the holder base 54 (as well as the junction between the base interface 53 and the holder base 54) at around 50° C. or less while the test subject stage 110 is heated to around 400° C. or greater. In still another example, simultaneously measuring the parameter of the test subject includes simultaneously imaging the test subject, for instance with a transmission electron microscope, along with mechanical testing and holding of the test subject statically. In still another example, mechanical testing, holding the test subject statically and simultaneously measuring the parameter of the test subject are performed within an imaging test subject holder 55 housed in an imaging device 96. One example of a test subject holder 54 is shown in FIGS. 6B and 7.

Figure 16A:
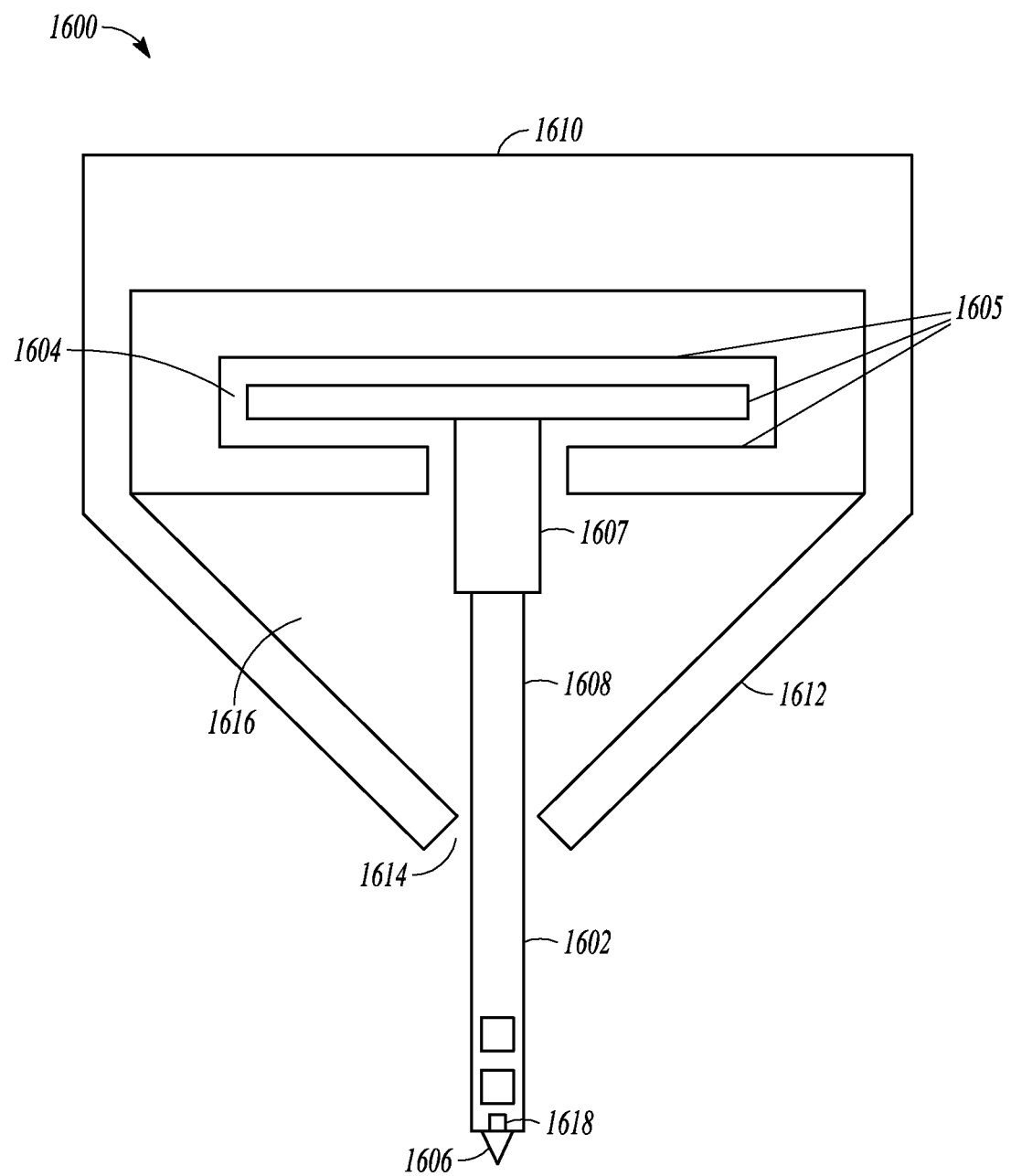
FIG. 16A is a schematic diagram showing one example of a heated mechanical testing tip assembly.
Figure 16B:
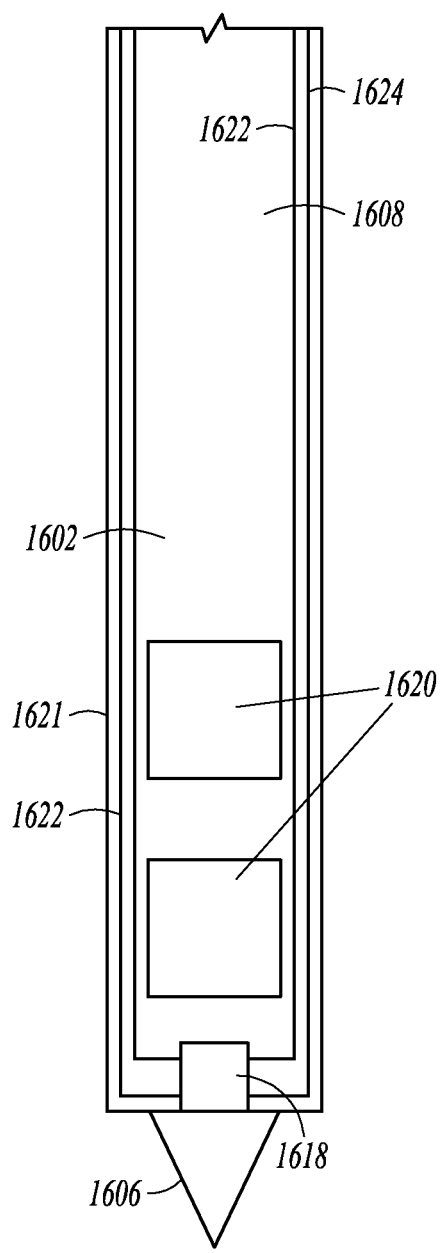
FIG. 16B is a detailed schematic diagram of the heated mechanical testing tip assembly shown in FIG. 16A.

Referring now to FIGS. 16A and 16B, one example of an instrument assembly 1600 is shown, including a tip heater assembly 1618. The instrument assembly 1600 includes a tip assembly 1602 having the tip heater assembly 1618, a tip 1606, such as a diamond tip, and an extension shaft 1608. In one example, the extension shaft 1608 includes, but is not limited to, a quartz tip extension having a minimal coefficient of thermal expansion and a minimal thermal conductivity. The instrument assembly 1600 further includes a transducer assembly 1604 including a two or more capacitor plates 1605 configured to measure movement of the tip assembly 1602 (e.g., the tip 1606) and also perform mechanical testing on a sub-micron scale (e.g., nano-scale) such as indentation, scratching and the like. In another example, the instrument assembly 1600 includes instruments to measure tension, compression, fracture testing and the like. The transducer assembly 1604 measures movement of the tip 1606 and also is capable of moving the tip 1606 for mechanical testing (such as indentation). The tip assembly 1602 is coupled with the transducer assembly 1604 by an interconnect 1607 extending therebetween. In one example, the interconnect 1607 is constructed with, but not limited to, materials including MACOR®, ZERODUR® and the like. As with the extension shaft 1608, the interconnect 1607 is constructed with materials having low coefficients thermal expansion and minimal thermal conductivities. The instrument assembly 1600 further includes a tip base 1610 (e.g., heat sink) sized and shaped to couple with an instrument including, but not limited to, scanning microscopes, electron microscopes, optical microscopes and the like.

Referring again to FIG. 16A, the extension shaft 1608 is shown extending through a heat shield orifice 1614 of a heat shield 1612. As shown, the extension shaft 1608 as well as the interconnect 1607 are positioned within a heat shield cavity 1616 of the instrument assembly 1600. In one example, the heat shield 1612 is a convective heat shield including inlet and outlet ports for transmission of refrigerant fluids including chilled water, glycol, ammonia and the like. In another example, the heat shield 1612 is constructed with materials having low coefficients of thermal expansion and minimal thermal conductivities. In still another example, the heat shield 1612 is coupled with a heat sink that forms the tip base 1610. The tip base is constructed with similar materials (with low thermal conductivities and coefficients of thermal expansion) to substantially prevent heat transfer from the instrument assembly 1600 to a coupled instrument, such as a microscope. The heat shield 1612 minimizes convective and radiative heat transfer from the tip heater assembly 1618 as well as the MEMS heater 100 as previously described herein. Throttling of heat transfer from the tip heater assembly 1618 as well as the MEMS heater 100 into the instrument assembly 1600 including the transducer assembly 1604 substantially minimizes any thermal expansion and drift of the transducer assembly 1604 and the extension shaft 1608.

Referring now to FIG. 16B, the tip heater assembly 1618 is shown in detail. The tip heater assembly 1618 includes a heating element and a sensor positioned immediately adjacent to the tip 1606. In one example, the heating element and the sensor are resistive heating and sensing elements. Positioning of the heating element and sensor immediately adjacent to the tip 1606 localizes heating of the tip assembly 1602 to the volume immediately adjacent to the tip 1606. The tip 1606 as well as the tip heater assembly 1618 are positioned remotely from the remainder of the extension shaft 1608 by voids 1620 interposed between the tip heater assembly 1618 and the remainder of the shaft. The voids 1620, as shown in FIG. 16B, are bounded by support columns 1621 extending between along the extension shaft 1608 to the tip heater assembly 1618. Sensor leads 1622 and heating element leads 1624, in on example, extend through the extension shaft 1608 including the support columns 1621 for electrical coupling with the tip heater assembly 1618.

In a similar manner to the MEMS heater 100, the instrument assembly 1600 including the tip heater assembly 1618 heats the tip 1606 locally without undesirable significant heat transfer through the remainder of the extension shaft 1608 and transducer assembly 1604. The tip heater assembly 1618 is remotely positioned relative to the remainder of instrument assembly 1600 and is immediately adjacent to the tip 1606. Further, because the tip heater assembly 1618 and tip 1606 are isolated from the remainder of the extensions shaft 1608 by the voids 1620 and the support columns 1621 heat transfer from the tip heater assembly 1618 is substantially throttled into the remainder of the extension shaft 1608. The support columns 1621 minimize conductive heat transfer through minimal cross-sectional area into the portion of the extension shaft 1608 coupled with the interconnect 1607 and the transducer assembly 1604 (see FIG. 16A). Additionally, the voids 1612 prevent any conduction of heat across the voids and substantially retard heat transfer by only allowing convective heat transfer (a minimal form of heat transfer relative to conductive heat transfer) and radiative heat transfer. In one example, where the instrument assembly 1600 is retained within a vacuum the voids 1620 substantially prevent any convective heat transfer from the tip heater assembly 1618 to the remainder of the extension shaft 1608 and only allow minimal radiative heat transfer across the voids. Additionally, because the extension shaft 1608 is constructed with materials having low coefficients of thermal expansion and minimal thermal conductivity heat transfer from the tip heater assembly 1618 to the remainder of the instrument assembly 1600 is minimized and corresponding thermal expansion and thermal drift of those components (the transducer assembly 1604 and a majority of the extension shaft 1608) are correspondingly minimized as well.

By localizing heating of the tip 1606 at the tip heater assembly 1618 only a small volume of the extension shaft 1608 relative to the entire extension shaft is heated with minimal heating power. Stated another way, minimal power is needed to heat the small volume of the tip heater assembly 1618, the portion of the extension shaft 1608 adjacent to the tip heater assembly 1618 and the tip 1606 relative to the larger volume of the remainder of the extension shaft 1608 and the instrument assembly 1600. The low volume and minimal heating power facilitate rapid thermal stabilization and minimize the thermal drift during mechanical testing and observation. Further, because the extension shaft 1608 positions the tip 1606 remotely relative to the transducer assembly 1604 as well as the of the instrument assembly 1600 thermal drift of the transducer assembly 1604 and the tip base 1610 is substantially minimized through use of the materials of the extension shaft, the geometry of the tip assembly 1602 as well as the heat shield 1612. Moreover, the geometry of the shaft including the support columns 1621 and the volume of the extension shaft 1608 including the tip heater assembly 1618 supports the tip 1606 and provides rigid support to ensure accurate transmission of forces from the transducer and measurement of movement of the tip 1606.

In an example where the instrument assembly 1600, including the tip heater assembly 1618, is incorporated into a system having a sample heating stage, such as the MEMS heater 100 described herein, the tip 1606 is heated to a temperature identical (or nearly identical) to the temperature of the sample stage having the MEMS heater and the sample thereon. Undesirable heat transfer from the heated sample to an otherwise cool tip is thereby substantially prevented. Stated another way, by substantially equalizing the temperatures of the tip 1606, the sample and the sample stage heat transfer between the tip 1606 and the sample is substantially prevented. Correspondingly, distortion of the sample and the mechanical properties measured from sample are substantially prevented. In other devices, contact between an unheated tip and a heated sample transfers heat from the heated sample into the tip causing distortions (thermal expansion, drift and the like) in one or more of the sample and the tip thereby distorting the properties and measurements collected by the tip.

In one example, the tip heater assembly 1618 is constructed with fabrication processes including MEMS process. For instance, the instrument assembly 1600 is constructed with but not limited to, focused ion beam lithography and milling, laser machining, photo lithography and etching (dry or wet) and the like. In another example, the instrument assembly 1600 including the tip heater assembly 1618 is provided together with the MEMS heater examples previously described herein. In still another example, the instrument assembly 1600 is provided separately from the heated test subject stage described herein.

CONCLUSION

The sample stage including the MEMS heater described herein and shown in the Figures mounts a small test sample and substantially statically holds the test sample in place when the temperature of the sample and the sample stage are raised and the sample is indented or compressed for material testing. The sample stage includes materials having high thermal resistances and low coefficients of thermal expansion that focus heating of the sample stage near the test sample and arrest heating of other portions of the stage and the test subject holder mounting the sample stage. Undesirable thermal expansion and drift of the sample stage are thereby minimized Further thermal expansion and drift of the test subject holder are minimized because heat transfer is throttled from the sample stage toward the test subject holder. The test subject holder is substantially larger than the sample stage and because of the arresting of heat transfer corresponding large amounts of thermal expansion and drift are prevented. Similarly, because the sample stage is relatively small compared to the test subject holder heating focused in the sample stage causes corresponding negligible drift in components that already have low coefficients of thermal expansion.

Further, the sample stage (e.g., including the stage plate separately or integrally formed with the sample stage) provides a stiff brace against deflection from testing indentations and compression and thereby ensures displacement and force measurements from indentation or compression do not include errors from deflection of the stage as opposed to indentation of the test sample. In contrast to heaters including membrane features, the sample stage described herein provides a solid and robust support for the test sample. At elevated temperatures (around 1000 degrees Celsius) the sample stage braces the test sample and is substantially free of deflection inaccuracies in nano-mechanical tests due to mechanical compliance in the stage. A combination of geometry of the sample stage—including the support columns and the robust front face—along with materials having stiffness (e.g., high young's modulus, flexural modulus and the like) ensures the sample stage is resistant to deflection over a range of operating temperatures for the MEMS heater.

Although the present disclosure has been described in reference to preferred embodiments, persons skilled in the art will recognize that changes may be made in form and detail without departing from the spirit and scope of the present disclosure. It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the present disclosure should, therefore, be determined with reference to the appended claims, along with the full scope of equivalents to which such claims are entitled.

What is claimed is:

1. A micron scale heating stage configured for conducting nanomechanical property testing comprising:
   a base interface configured for coupling with a holder base of a sub-micron mechanical property testing instrument and electro-mechanical transducer assembly; and
   a test subject stage extending from the base interface, the test subject stage includes:
      a stage subject surface outside of an electron beam of a transmission electron microscope when the micron scale heating stage is installed within a transmission electron microscope, the stage subject surface substantially statically positions a test subject location of a test subject both within the electron beam and along a testing instrument axis of the sub-micron mechanical property testing instrument, while the stage subject surface is both offset from the electron beam and intercepts the testing instrument axis, a stage plate underlying the stage subject surface and outside of the electron beam, the stage plate braces the stage subject surface, and a heating element on the test subject stage and interposed between the stage subject surface and the stage plate, and the holder base is thermally isolated from the heating element.

2. The micron scale heating stage of claim 1, wherein a test subject stage volume is less than a holder base volume.

3. The micron scale heating stage of claim 1, wherein the test subject stage is heatable from a cold state to a heated state, and in the heated state the heating element on the test subject stage conducts heat through the test subject stage to a test subject and elevates the temperature of the test subject to a specified temperature, and heat transfer into the base interface from the test subject stage is substantially arrested according to the cross sectional area between the base interface and the test subject stage, a test subject stage thermal resistance and a void between the test subject stage and the base interface, and the test subject is substantially located at a static location during heating according to the arrested heat transfer.

4. The micron scale heating stage of claim 1 comprising at least one support coupled between the base interface and the test subject stage, and the at least one support has a cross sectional area perpendicular to a direction from the test subject stage to the base interface smaller than or equal to a cross sectional area of the test subject stage perpendicular to the same direction.

5. The micron scale heating stage of claim 1, wherein the support includes one or more voids between the test subject stage including the heating element and the holder base.

6. The micron scale heating stage of claim 1, wherein while the test subject stage is in a heated state at an elevated temperature greater than or equal to around 400 degrees Celsius a juncture between the base interface and a holder base is below around 50 degrees Celsius according to the thermal isolation between the test subject stage and the base interface.

7. The micron scale heating stage of claim 1, wherein the heating element is a resistive heating element.

8. The micron scale heating stage of claim 1, wherein the heating element underlies the stage subject surface.

9. The micron scale heating stage of claim 1 comprising a temperature sensing resistive element on the test subject stage adjacent to the stage subject surface.

10. The micron scale heating stage of claim 1, wherein the stage subject surface and the stage plate are integral.

11. The micron scale heating stage of claim 1, wherein the heating element is immediately adjacent to the stage subject surface.

12. A sub-micron scale property testing apparatus comprising:
a test subject holder and heating assembly, the test subject holder and heating assembly includes:
a holder base configured to couple with a sub-micron scale property testing instrument and electro-mechanical transducer assembly; and
a sample stage extending from with the holder base, the holder base supporting the sample stage thereon, the sample stage includes:
a base interface coupled with the holder base,
a test subject stage coupled with the base interface, the base interface interposed between the test subject stage and the holder base, and the test subject stage is thermally isolated from the holder base, the test subject stage includes:

a stage subject surface configured to receive a test subject,
a stage plate bracing the stage subject surface, the stage plate is under the stage subject surface and extends across the stage subject surface,
wherein, when the sample stage is installed in a transmission electron microscope the stage subject surface positions the test subject within a transmission electron beam, the stage subject surface and the stage plate are both offset from the electron beam and the stage subject surface intercepts a testing instrument axis of the sub-micron scale property testing instrument, and
a heating element on the test subject stage and adjacent to the stage subject surface and the stage plate, the heating element is configured to generate heat at the stage subject surface, and
at least one support extending from the base interface to the stage subject surface and the heating element, the at least one support has a cross sectional area perpendicular to a direction from the base interface to the stage subject surface smaller or equal to a cross sectional area of the test subject stage perpendicular to the same direction.

13. The sub-micron scale property testing apparatus of claim 12, wherein the sub-micron mechanical testing instrument and electro-mechanical transducer assembly includes one or more of indentation, compression, tensile, fatigue, tribology and fracture instruments.

14. The sub-micron scale property testing apparatus of claim 12, wherein the sub-micron scale property testing instrument and electro-mechanical transducer assembly includes a force actuator and a displacement sensor.

15. The sub-micron scale property testing apparatus of claim 12, wherein the heating element is a resistive heating element.

16. The sub-micron scale property testing apparatus of claim 12 comprising a temperature sensing resistive element on the test subject stage adjacent to the stage subject surface.

17. The sub-micron scale property testing apparatus of claim 12, wherein the stage subject surface and the stage plate are integral.

18. The sub-micron scale property testing apparatus of claim 12, wherein the at least one support includes one or more voids between the test subject stage and the base interface.

19. The sub-micron scale property testing apparatus of claim 12, wherein the holder base is at a temperature of 50 degrees Celsius or less when the test subject stage is heated by the heating element to a temperature of around 400 degrees Celsius according to the thermal isolation between the test subject stage and the holder base.

20. The sub-micron scale property testing apparatus of claim 12, wherein the heating element is immediately adjacent to the stage subject surface.

21. A sub-micron scale property testing apparatus comprising:
a test subject holder and heating assembly, the test subject holder and heating assembly includes:
a holder base configured to couple with a sub-micron mechanical testing instrument and electro-mechanical transducer assembly,
a test subject stage extending from the holder base, the test subject stage includes a stage plate, the test subject stage is configured to receive a test subject on a stage subject surface coupled with the stage plate, when installed within a transmission electron microscope the test subject stage is outside of an electron beam of the transmission electron microscope and the test subject stage statically positions a test subject location of a test subject both within the electron beam and along a testing instrument axis of the sub-micron mechanical property testing instrument while the stage subject surface is both offset from the electron beam and intercepts the testing instrument axis, and the test subject stage is thermally isolated from the holder base, and a heating element on the test subject stage and interposed between the stage subject surface and the stage plate, wherein the heating element is configured to generate heat at the stage subject surface.

22. The sub-micron scale property testing apparatus of claim 21, wherein the heating element is a resistive heating element.

23. The sub-micron scale property testing apparatus of claim 21 comprising at least one support coupled between the holder base and the test subject stage, and the at least one support has a cross sectional area smaller perpendicular to a direction from the test subject stage to the holder base than a cross sectional area of the test subject stage perpendicular to the same direction.

24. The sub-micron scale property testing apparatus of claim 21, wherein the stage plate and the stage subject surface are integral.

25. The sub-micron scale property testing apparatus of claim 21, wherein stage subject surface is includes a sample mount coupled along the stage plate, and the sample mount has a thermal conductivity much greater than a stage thermal conductivity and evenly distributes heat from the test subject stage through the sample mount.

26. The sub-micron scale property testing apparatus of claim 21, wherein the stage plate braces the stage subject surface against deflection caused by mechanical testing of a sample on the stage subject surface.

27. The sub-micron scale property testing apparatus of claim 21, wherein the heating element is immediately adjacent to the stage subject surface.

28. The sub-micron scale property testing apparatus of claim 21, wherein the heating element is within the test subject stage.

29. The sub-micron scale property testing apparatus of claim 21, wherein the stage subject surface is parallel to the electron beam.

30. A sub-micron scale property testing apparatus comprising:
a test subject holder and heating assembly configured to couple with a transmission electron microscope and a sub-micron mechanical property testing instrument having a testing instrument axis, the test subject holder and heating assembly includes:
a holder base configured for coupling with the transmission electron microscope and the sub-micron mechanical property testing instrument,
a sample stage extending from the holder base, the holder base supporting the sample stage thereon, the sample stage includes:
a base interface coupled with the holder base,
a means for holding a test subject coupled with the base interface, the base interface interposed between the holder base and the means for holding, the means for holding includes a subject surface configured to receive a subject, the means for holding the test subject is both outside of an electron beam of a transmission electron microscope when the test subject holder is installed in the transmission electron microscope and intercepts the testing instrument axis, and the means for holding the test subject positions the test subject within the electron beam, the means for holding includes a plate beneath the subject surface,
a means for heating both a test subject and the subject surface, the means for heating is interposed between the subject surface and the plate, and the means for heating generates heat at the means for holding, and
at least one support extending from the base interface to the means for holding and the means for heating, the at least one support having a cross sectional area smaller than or equal to a cross sectional area of the means for holding, the at least one support thermally isolating the means for holding from the holder base.

31. The sub-micron scale property testing apparatus of claim 30, wherein the plate supports the subject surface against deflection from mechanical testing of a subject positioned on the subject surface.

32. The sub-micron scale property testing apparatus of claim 30, wherein a volume of the means for holding is smaller than a holder base volume, and when heated the means for heating generates heat at the means for holding beneath the subject surface.

33. The sub-micron scale property testing apparatus of claim 30, wherein the means for heating includes a resistive heating element on the means for holding the test subject, and the resistive heating element is thermally isolated from the holder base.

34. The sub-micron scale property testing apparatus of claim 30 comprising one or more of:
a void interposed between the means for holding and the base interface,
the means for holding including a material having low thermal conductivity, and
one or more of the material, the void and the at least one support throttles heat transfer from the means for holding to the holder base and maintains the holder base near 50 degrees Celsius or less when the means for holding is heated to around 400 degrees Celsius or greater.

35. A method of sub-micron scale mechanical testing of a test subject, the method comprising:
coupling a test subject along a stage subject surface of a test subject stage, the test subject stage extending from a holder base;
coupling the holder base within a sub-micron scale mechanical testing instrument and electro-mechanical transducer assembly, at least the test subject stage is outside of an electron beam axis when the electro-mechanical transducer assembly is installed in a transmission electron microscope;
heating the test subject to a specified temperature through heat generated at the test subject stage adjacent to the test subject by a heating element;
mechanically testing the test subject at a test subject location on a micrometer or less scale;
bracing the stage subject surface against deflection from mechanically testing with a stage plate extending across the stage subject surface; and
holding the test subject statically against thermal mechanical drift and expansion from the heating by throttling heat transfer from the test subject stage to the holder base, holding includes:

statically positioning the test subject location within the electron beam with the test subject stage while the test subject stage is offset from the electron beam, and at the same time statically positioning the test subject location along a testing instrument axis of the sub-micron scale mechanical testing instrument while the test subject stage intercepts the testing instrument axis.

36. The method of claim 35, wherein coupling the test subject along the stage subject surface includes mounting the test subject on a sample mount, and coupling the sample mount with the test subject stage.

37. The method of claim 36, wherein heating the test subject to the specified temperature includes equally distributing heat throughout the sample mount.

38. The method of claim 35 comprising sensing the temperature of the test subject stage with a sensing element positioned at the test subject stage.

39. The method of claim 38, wherein heating the test subject to the specified temperature includes controlling heating of the test subject with a closed or open loop control system including the heating element and a sensing element at the test subject stage.

40. The method of claim 35, wherein heating the test subject to the specified temperature includes heating only a test subject stage volume and the test subject.

41. The method of claim 35, wherein throttling heat transfer to the holder base includes one or more of:

throttling heat transfer through one or more supports, the one or more supports having a smaller cross sectional area along a direction of heat transfer from the test subject stage to the holder base smaller compared to a test subject stage cross sectional area in the same direction, throttling heat transfer through the test subject stage, where the test subject stage has a first thermal resistance greater than a second thermal resistance of a holder base, and throttling heat transfer across a void interposed between the test subject stage and the holder base.

42. The method of claim 35, wherein throttling heat transfer to the holder base includes maintaining the holder base at around 20 degrees Celsius while the test subject stage is heated to around 400 degrees Celsius or greater.

43. The method of claim 35, wherein simultaneously measuring the parameter of the test subject includes simultaneously imaging the test subject with the mechanical testing and holding of the test subject statically.

44. The method of claim 35, wherein mechanical testing, holding the test subject statically and simultaneously measuring the parameter of the test subject are performed within an imaging test subject holder housed in an imaging device.

* * * * *